United States Patent [19]

Therien et al.

[11] Patent Number: 5,371,199

[45] Date of Patent: Dec. 6, 1994

[54] SUBSTITUTED PORPHYRINS, PORPHYRIN-CONTAINING POLYMERS, AND SYNTHETIC METHODS THEREFOR

[75] Inventors: Michael J. Therien; Stephen G. DiMagno, both of Philadelphia, Pa.

[73] Assignee: The Trustees of the University of Pennsylvania, Philadelphia, Pa.

[21] Appl. No.: 929,943

[22] Filed: Aug. 14, 1992

[51] Int. Cl.$^5$ .................. C07D 487/22; C01F 17/00; C01G 55/00

[52] U.S. Cl. ........................................ 534/11; 534/15; 540/145

[58] Field of Search ...................... 540/145; 534/11.15

[56] References Cited

U.S. PATENT DOCUMENTS

| | | | |
|---|---|---|---|
| 3,687,863 | 8/1972 | Wacher | 252/300 |
| 3,897,255 | 7/1975 | Erickson | 96/115 |
| 3,899,334 | 8/1975 | Erickson | 96/48 |
| 4,360,703 | 11/1982 | Bolton et al. | 136/263 |
| 4,647,478 | 3/1987 | Formanek et al. | 427/164 |
| 4,668,670 | 5/1987 | Rideout et al. | 514/185 |
| 4,792,836 | 12/1988 | Quinlan | 357/30 |
| 4,895,682 | 1/1990 | Ellis et al. | 540/145 |
| 4,957,615 | 9/1990 | Ushizawa et al. | 204/415 |
| 4,986,256 | 1/1991 | Cohen et al. | 128/653 |
| 4,988,808 | 1/1991 | Morgan et al. | 534/11 |
| 5,164,944 | 11/1992 | Benton et al. | 371/40.1 |
| 5,171,741 | 12/1992 | Dougherty | 514/185 |
| 5,252,730 | 10/1993 | Mackey | 540/140 |

FOREIGN PATENT DOCUMENTS

| | | |
|---|---|---|
| 0161606A2 | 6/1985 | European Pat. Off. |
| 0168994A2 | 6/1985 | European Pat. Off. |
| 0172427A2 | 7/1985 | European Pat. Off. |
| 0340968 | 4/1989 | European Pat. Off. |
| 0384503A1 | 1/1990 | European Pat. Off. |
| 0390523A2 | 3/1990 | European Pat. Off. |
| 0393575A1 | 4/1990 | European Pat. Off. |
| 0428214A1 | 11/1990 | European Pat. Off. |
| 0442060A2 | 11/1990 | European Pat. Off. |
| WO85/01617 | 4/1985 | WIPO |
| WO87/00023 | 1/1987 | WIPO |
| WO89/10772 | 11/1989 | WIPO |
| WO89/11277 | 11/1989 | WIPO |
| WO91/04029 | 4/1991 | WIPO |
| WO91/07659 | 5/1991 | WIPO |
| WO91/09631 | 7/1991 | WIPO |
| 91/09631 | 7/1991 | WIPO |

OTHER PUBLICATIONS

Callot, Chemical Abstracts, vol. 81, 1974 Abstract 105479p.

Yang et al. Chemical Abstracts, vol. 105, 1986 Abstract 180709f.

Pandey, R. K., et al., *Tetrahedron Letters*, 1990, 31, 7399–7402.

Maruyama, et al., *Bull. Chem. Soc. Jpn.*, 1990, 63, 170–175.

Nagata, T., et al., *J. Am. Chem. Soc.*, 1990, 112, 3054–3059.

Vicente et al., *J. Org. Chem.*, 1991, 56, 4407–4418.

Wallace, et al., *Tetrahedron Letters*, 1990, 31, 7265–7268.

Pandey, R. K., et al., *Tetrahedron Letters*, 1990, 31, 789–792.

Pandey, R. K., et al., *Tetrahedron Letters*, 1992, 33, 5315–5318.

Helms, A., et al., *J. Am. Chem. Soc.*, 1992, 114, 6227–6238.

Morris, I. K., et al., *J. Am. Chem. Soc.*, 1990, 50, 1231–1236.

(List continued on next page.)

*Primary Examiner*—Mukund J. Shah
*Assistant Examiner*—P. K. Sripada
*Attorney, Agent, or Firm*—Woodcock Washburn Kurtz Mackiewicz & Norris

[57] ABSTRACT

Porphyrins substituted with, for example, vinyl and acetylene groups are provided, along with polymers containing the same. In preferred embodiments, the substituted porphyrins are prepared by coupling halogenated porphyrins with carbon-centered anionic groups via metal-mediated crosscoupling reactions under stoichiometric or catalytic conditions.

44 Claims, 3 Drawing Sheets

OTHER PUBLICATIONS

Rodriguez, J., *J. Am. Chem. Soc.* 1991, 113, 1652–1659.
Nudy, Louis R., et al., *Tetrahedron*, 1984, 40, 2359–2363.
Gonsalves, Rocha, d'A. A. M. et al., *J. Heterocyclic Chem.*, 1985, 22, 931.
Bonnett, R., "Nomenclature," The Porphyrins, Dolphin, ed., vol. I, Academic Press, New York, 1978.
Mauzerall D., "The Porphyrinogens," The Porphyrins, Dolphin, ed., vol. I, Academic Pressi, New York, 1978.
Kim, et al., "Synthesis of Porphyrins from Monopyrroles," The Porphyrins, Dolphin, ed., vol. III, Academic Press, New York, 1978.
Paine, "Synthesis of Pyrroles and of Porphyrins via Single–Step Coupling of Dipyrrolic Intermediates," The Porphyrins, Dolphin, ed., vol. III, Academic Press, New 1978.
Johnson, A. W., "Synthesis of Porphyrins from 1,19–Dideoxybiladienes—ac and 1,19–Dideoxybilenes–b," The Porphyrins, Dolphin, ed., vol. III, Academic Press, New 1978.
Kumada, M., *Pure & Appl. Chem.*, 1980, 52, 660–679.
Collman, J. P. et al., *"University Science Books,"* 1987 Chapter 14, Mill Valley, Calif.
Hayashi, T., et al., *Tetrahedron Letters*, 1979, 21, 1871–1874.
Stein, C. A. et al., *Cancer Research*, 1988, 2659–2668.
Lindsey, Jonathan S., et al. *J. Org. Chem.*, 1987, 52, 836.
Cohen, Jack S., "Use of Paramagnetic Metalloporphyrins as Contrast Agents for Tumors in NMR Imaging," (Feb. 1985). U.S. Department of Commerce, Springfield Va. 22161.
Manka, John S., et al., *Tetrahedron Letters*, 1989, 30, 7341–7344.
Wytko, Jennifer A., et al., *J. Org. Chem.*, 1992, 57, 1015–1018.
Lindsey, Jonathan S., et al., *J. Org. Chem.*, 1988, 54, 828–836.
Clezy, P. S., et al., "Synthesis of Porphyrins from Oxobilane Intermediates," The Porphyrins, Dolphin, ed., vol. III, Academic Press, New York, 1978.
DiNello, Robert K., et al., "Isolation and Modification of Natural Porphyrins," The Porphyrins, Dolphin, ed., vol. III, Academic Press, New York, 1978.
Godquin-Giroud Anne-Marie et al., "Metallomesogens: Metal Complexes in Organized Fluid Phases," Angew. Chem. Int. Ed. Engl. 30 (1991), 375–402.
Lehn, Jean-Marie, "Angewandte Chemie International Edition in Engish," vol. 27, No. 1, (Jan. 1988), pp. 89–112.
Wasielewski, Michael R., *Chem. Rev*, 1992, 92, 435–461.
Patai and Rapport, "The Chemistry of Functional Groups, Supplement C," part 1, pp. 529–534, Wiley, N.Y. (1983).
Eglinton and McCrae, Adv. Org. Chem. 4, 225–328, (1963).
Anderson, H. L. *Tetrahedron Letters*, 1992, 33, 1101–1104.
Arnold et al., "Some Reactions of Meso–Formyloctaethylporphyrin", J.C.S. Perkin I, pp. 366–370. 1986.
Komarov et al., "Synthesis and Some Transformations of α–Siliconacetylenic Aldehydes", UDC, pp. 920–922 1965.
Hevesi, et al., *J. Org. Chem.*, 1991, 56, 4407–4418.
Gunter et al., *Aust. J. Chem.*, 1990, 43, 1839–60.
Patai and Rapport, "The Chemistry of Functional Groups Supplement C", Chapter 13, pp. 513 (1983).
Osuka, et al., *Angew. Chem. Int. Ed. Engl.*, 1991, 30, 582.
Groves, et al., *J. Am. Chem. Soc.*, 1983, 105, 5791.
Mansuy, et al., *J. Chem. So. Chem. Commun.*, 1985, 155–156.
Durand et al., *J. Am. Chem. Soc.*, 1983, 105, 2710–2718.
Minnetian, O. M., *J. Org. Chem.*, 1989, 54, 5567–5574.

SUBSTITUTED PORPHYRINS, PORPHYRIN-CONTAINING POLYMERS, AND SYNTHETIC METHODS THEREFOR

FIELD OF THE INVENTION

This invention relates to substituted porphyrins and to techniques and intermediates useful in preparing substituted porphyrins. The invention also relates to polymers and macromolecules prepared from the porphyrins, and to new and improved uses for the porphyrins and their polymers.

BACKGROUND OF THE INVENTION

Porphyrins are derivatives of porphine, a conjugated cyclic structure of four pyrrole rings linked through their 2- and 5-positions by methine bridges. Porphyrins can be covalently attached to other molecules. The electronic features of the porphyrin ring system can be altered by the attachment of one or more substituents. The term "porphyrin" includes derivatives wherein a metal atom is inserted into the ring system, as well as molecular systems in which ligands are attached to the metal. The substituents, as well as the overall porphyrin structure, can be neutral, positively charged, or negatively charged.

Numerous porphyrins have been isolated from natural sources. Notable porphyrin-containing natural products include hemoglobin, the chlorophylls, and vitamin $B_{12}$. Also, many porphyrins have been synthesized in the laboratory, typically through condensation of suitably substituted pyrroles and aldehydes. However, reactions of this type generally proceed in low yield, and cannot be used to produce many types of substituted porphyrins.

Accordingly, there exists a need in the art for synthetic methods capable of producing a greater variety of porphyrins than presently available.

OBJECTS OF THE INVENTION

It is one object of the present invention to provide improved methods for synthesizing substituted porphyrins.

It is another object of the invention to provide novel substituted porphyrins.

It is yet another object to provide novel porphyrin-containing compounds.

It is a further object of the invention to provide polymers containing linked porphyrin units.

It is still another object to provide new applications for substituted porphyrins and porphyrin-containing compounds.

SUMMARY OF THE INVENTION

These and other objects are satisfied by the present invention, which provides porphyrins having formula (1) and (2):

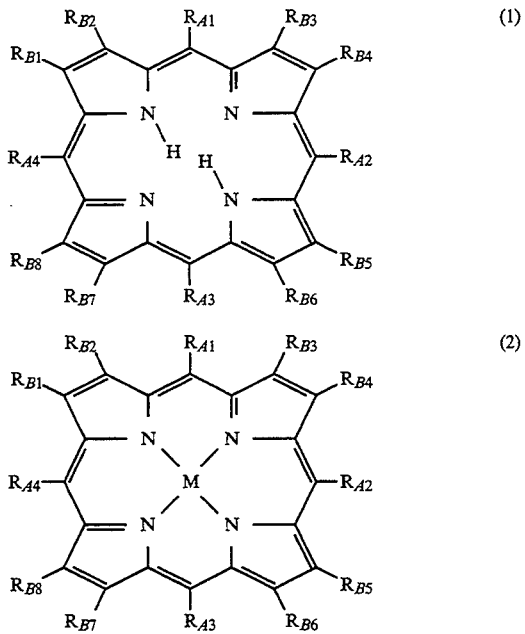

wherein M is a chelated metal atom and $R_{A1}$-$R_{A4}$ and $R_{B1}$-$R_{B8}$ are, independently, H or chemical functional groups that can bear a carbon-centered negative charge. In certain preferred embodiments, at least one of $R_{A1}$-$R_{A4}$ has formula CH=$CH_2$ or at least one of $R_{A1}$-$R_{A4}$ or $R_{A1}$-$R_{B8}$ has formula C($R_C$)=C($R_D$)($R_E$), provided that at least one of $R_C$, $R_D$, and $R_E$ is not H, where $R_C$, $R_D$, and $R_E$ are, independently, H, F, Cl, Br, I, alkyl or heteroalkyl having from 1 to about 20 carbon atoms, aryl or heteroaryl having about 6 to about 20 carbon atoms, alkenyl or heteroalkenyl having from 1 to about 20 carbon atoms, alkynyl or heteroalkynyl having from 1 to about 20 carbon atoms, trialkylsilyl or porphyrinato; M is a transition metal, a lanthanide, actinide, rare earth or alkaline metal. $R_C$, $R_D$, and $R_E$ also can include peptides, nucleosides, and/or saccharides.

In other preferred embodiments, at least one of $R_{A1}$-$R_{A4}$ or $R_{B1}$-$R_{B8}$ has formula C=C($R_D$). In further preferred embodiments, at least one of $R_{A1}$-$R_{A4}$ is haloalkyl having from 1 to about 20 carbon atoms. In further preferred embodiments, at least one of $R_{B1}$-$R_{B8}$ is haloalkyl having 2 to about 20 carbon atoms or at least at least five of $R_{B1}$-$R_{B8}$ are haloalkyl having from 1 to about 20 carbon atoms or haloaryl having from about 6 to about 20 carbon atoms. In further preferred embodiments, at least one of $R_{B1}$-$R_{B8}$ is haloaryl or haloheteroaryl having about 6 to about 20 carbon atoms. In still further preferred embodiments, at least one of $R_{A1}$-$R_{A4}$ or $R_{B1}$-$R_{B8}$ includes an amino acid, peptide, nucleoside, or saccharide.

The present invention also provides processes and intermediates for preparing substituted porphyrins. In certain embodiments, the processes comprise providing a porphyrin compound having formula (1) or (2) wherein at least one of $R_{A1}$-$R_{A8}$ or $R_{B1}$-$R_{B8}$ is a halogen and contacting the porphyrin compound with a complex having formula Y(L)$_2$ wherein Y is a metal and L is a ligand. This produces a first reaction product, which is contacted with an organometallic compound having general formula T($R_L$)$_z$($R_O$), T($R_L$)$_z$($R_O$)$_y$($X_B$)$_w$, T($R_O$)($X_B$) or T($R_O$)$_y$ where T is a metal; $X_B$ is a halogen; $R_L$ is cyclopentadienyl or aryl having about 6 to about 20 carbon atoms; $R_O$ is alkyl, alkenyl or alkynyl having 1 to about 10 carbon atoms, and having about 6 to about 20 carbon atoms; z and w are greater than or equal to 0; and y is at least 1. This contacting produces a second reaction product which, through reductive elimination, yields a third reaction product that contains a porphyrin substituted with $R_O$.

In another aspect, the invention provides polymers comprising linked porphyrin units. In certain embodiments, each of the porphyrin units, independently, has formula (1) or (2) wherein at least one of $R_{A1}$-$R_{A4}$ or $R_{B1}$-$R_{B8}$ function as linking groups. In preferred embodiments, at least a portion of a linking group has formula $[C(R_C)=C(R_D)(R_E)]_x$, $[C=C(R_D)]_x$, $[CH_2(R_C)—CH(R_D)(R_E)]_x$ or $[CH=CH(R_D)]_x$ where x is at least 1. The remaining of $R_{A1}$-$R_{A4}$ and $R_{B1}$-$R_{B8}$ can be H, halogen, alkyl or heteroalkyl having 1 to about 20 carbon atoms or aryl or heteroaryl having 6 to about 20 carbon atoms, $C(R_C)=C(R_D)(R_E)$, $C=C(R_D)$, or a chemical functional group that includes a peptide, nucleoside, and/or saccharide. In other preferred embodiments, the linking group is cycloalkyl or aryl having about 6 to about 22 carbon atoms.

The invention also provides processes for preparing porphyrin-containing polymers. In certain embodiments, the processes comprise providing at least two compounds that, independently, have formula (1) or (2) wherein at least one of $R_{A1}$-$R_{A4}$ or $R_{B1}$-$R_{B8}$ in each of the compounds contains an olefinic carbon-carbon double bond or a chemical functional group reactive therewith. In other embodiments, at least one of $R_{A1}$-$R_{A4}$ or $R_{B1}$-$R_{B8}$ in each of the compounds contains a carbon-carbon triple bond or a chemical functional group reactive therewith. The compounds are then contacted for a time and under reaction conditions effective to form covalent bonds through the carbon-carbon double and/or triple bonds.

The porphyrins and porphyrin-containing polymers of the invention can be used, for example, as dyes, catalysts, contrast agents, antitumor agents, antiviral agents, and in chemical sensors and electrooptical devices.

BRIEF DESCRIPTION OF THE FIGURES

The numerous objects and advantages of the present invention may be better understood by those skilled in the art by reference to the accompanying figures, in which.

DETAILED DESCRIPTION OF THE INVENTION

Figure 1:
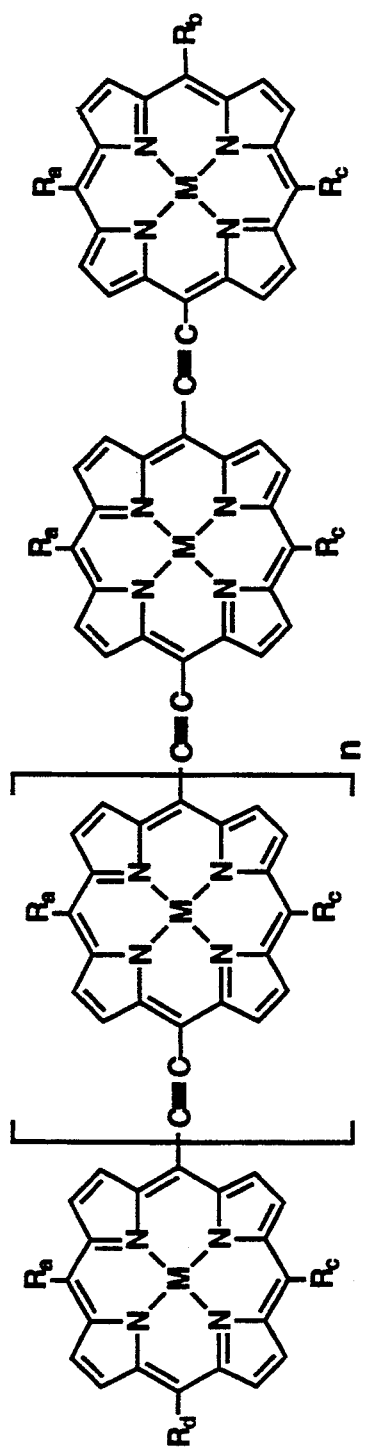
FIG. 1 shows a linear polymer of the invention having monoacetylenic linking groups.
Figure 2:
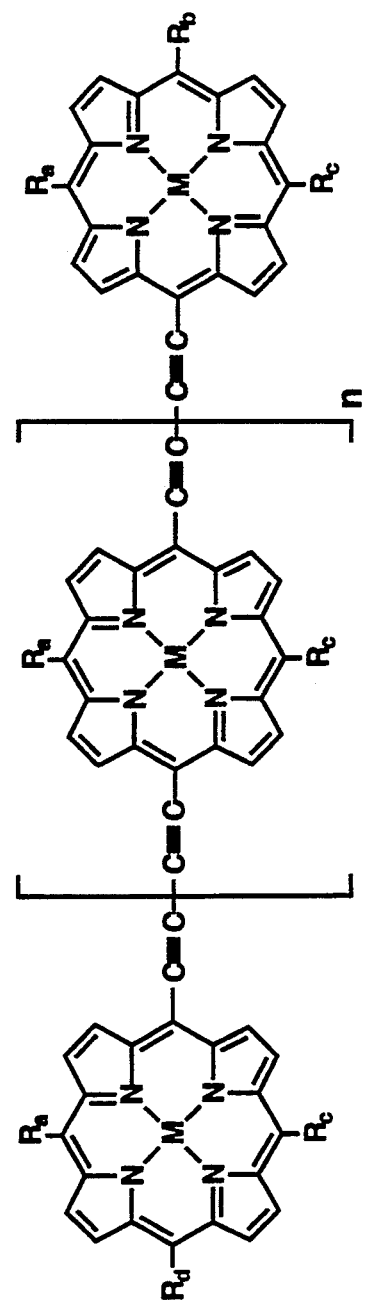
FIG. 2 shows a linear polymer of the invention having diacetylenic linking groups.
Figure 3:
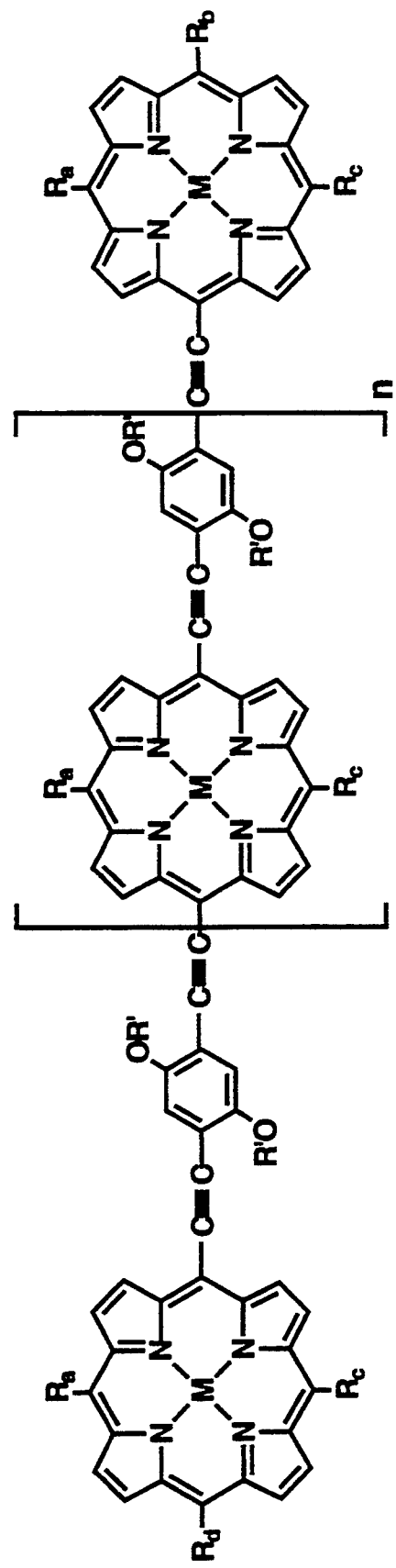
FIG. 3 shows a linear polymer of the invention having monoacetylenic and phenoxy linking groups, wherein R' is alkyl having from 1 to about 20 carbon atoms.
Figure 4:
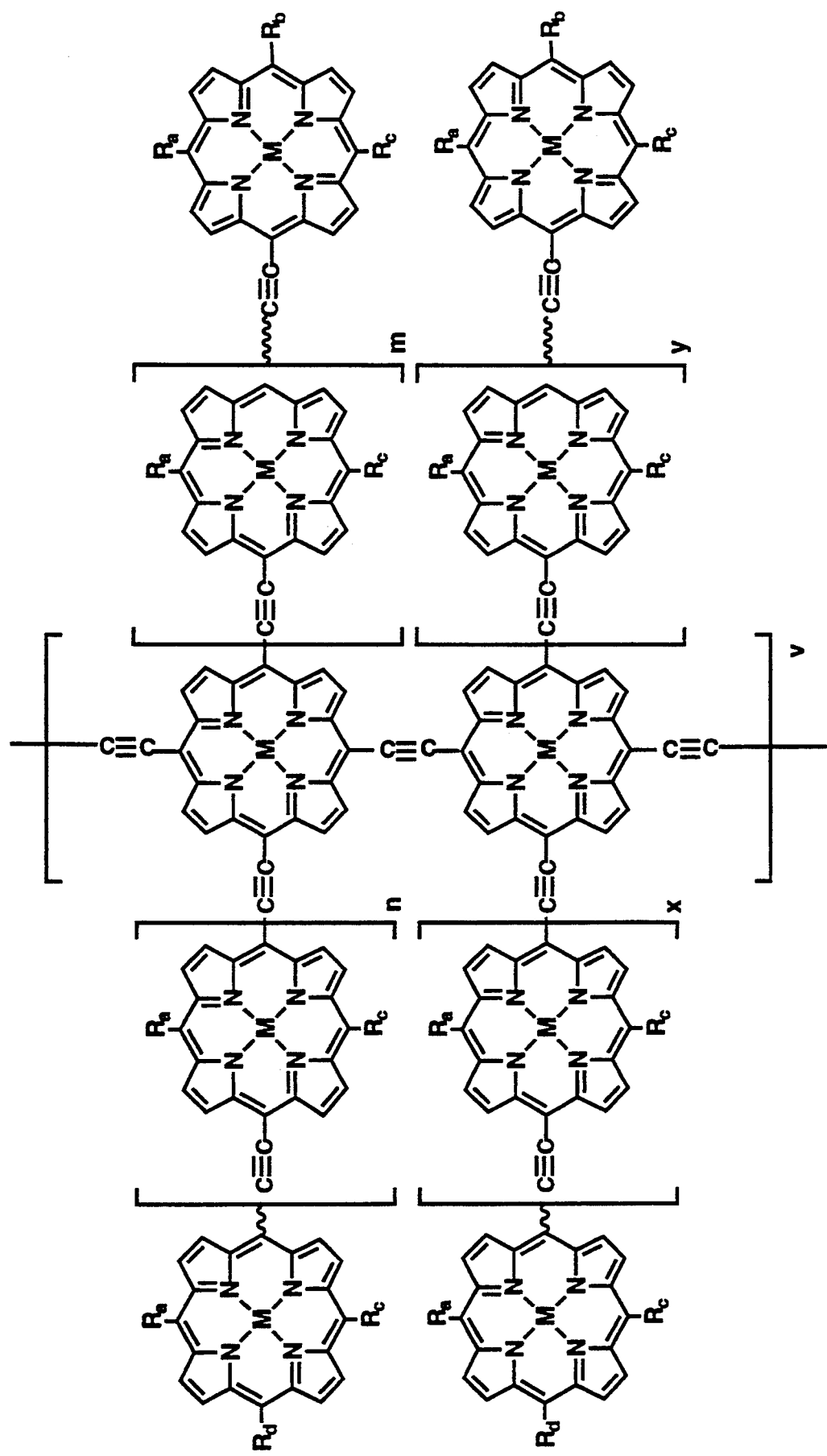
FIG. 4 shows a cross-linked polymer of the invention, wherein n, m, v, x, and y are at least 1.

It has been found in accordance with the present invention that a wide variety of novel porphyrins can be prepared through metal-mediated cross coupling of a halogenated porphyrin core and a suitable organometallic moiety. In general, the resulting porphyrins have formula (1) or (2):

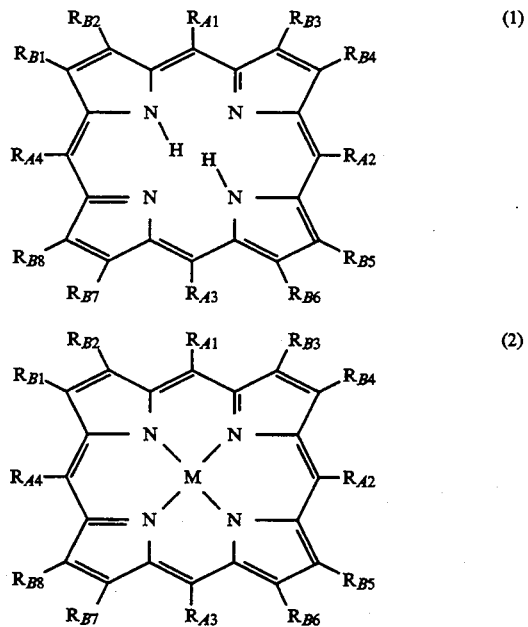

wherein M is a chelated metal atom and $R_{A1}$-$R_{A4}$ and $R_{B1}$-$R_{B8}$ are, independently, H or chemical functional group that can bear a carbon-centered negative charge (i.e., exist as a carbocentric anion in solution or otherwise). M preferably is a lanthanide or actinide or a metal such as Sc, Ti, V, Cr, Mn, Fe, Co, Ni, Cu, Y, Zr, Nb, Mo, Ru, Rh, Pd, Ag, La, Hf, Ta, W, Re, Os, Ir, Pt., Cd, Hg, Li or Au. More preferably, M is a metal having a full valence shell, even more preferably Zn or Mg.

$R_{A1}$-$R_{A4}$ and $R_{B1}$-$R_{B8}$ can be virtually any chemical functional group or covalent assemblage of functional groups capable of bearing a carbon-centered negative charge. Preferably, $R_{A1}$-$R_{A4}$ and $R_{B1}$-$R_{B8}$ are primary or secondary alkyl, alkenyl, haloalkenyl, alkynyl, haloalkynyl, aryl or heteroaryl. $R_{A1}$-$R_{A4}$ and $R_{B1}$-$R_{B8}$ should contain functionality that can withstand the reaction conditions associated with metal-mediated cross coupling. Those skilled in the art will recognize that chemical protecting groups can be attached to any sensitive functionality found within $R_{A1}$-$R_{A4}$ and $R_{B1}$-$R_{B8}$ and then removed after the coupling reactions have been completed.

Compounds having formulas (1) and (2) preferably bear 1, 2, 4, 8, or 12 substituents (i.e., 1, 2, 4, 8, or 12 of $R_{A1}$-$R_{A4}$ and $R_{B1}$-$R_{B8}$ are not H). More preferably, these compounds bear 2 or 4 substituents that contain alkenyl or alkynyl functionality.

In certain embodiments, at least one of $R_{A1}$-$R_{A4}$ has formula $CH=CH_2$. In other embodiments, at least one of $R_{A1}$-$R_{A4}$ or $R_{B1}$-$R_{B8}$ has formula $C(R_C)=C(R_D)(R_E)$, provided that at least one of $R_C$, $R_D$, and $R_E$ is not H, or at least one of $R_{A1}$-$R_{A4}$ or $R_{B1}$-$R_{B8}$ has formula $C=C(R_D)$. In further preferred embodiments, at least one of $R_{A1}$-$R_{A4}$ is haloalkyl having from 1 to about 20 carbon atoms. In further preferred embodiments, at least one of $R_{B1}$-$R_{B8}$ is haloalkyl having 2 to about 20 carbon atoms or at least five of $R_{B1}$-$R_{B8}$ are haloalkyl having from 1 to about 20 carbon atoms. In further preferred embodiments, at least one of $R_{B1}$-$R_{B8}$ is haloaryl or haloheteroaryl having about 6 to about 20 carbon atoms. Preferred halogenated moieties are fully halogenated (e.g., $CF_3$). In still further embodiments, at least one of $R_{A1}-R_{A4}$ or $R_{B1}-R_{B8}$ is a single amino acid or a terminal amino acid of a polypeptide.

$R_C$, $R_D$, and $R_E$ can be any of a wide variety of chemical functional groups. Preferably, $R_C$, $R_D$, and $R_E$ are, independently, H, F, Cl, Br, I, alkyl or heteroalkyl having from 1 to about 20 carbon atoms, aryl or heteroaryl having about 6 to about 20 carbon atoms, alkenyl or heteroalkenyl having from 2 to about 20 carbon atoms, alkynyl or heteroalkynyl having from 2 to about 20 carbon atoms, trialkylsilyl, or porphyrinato. The terms heteroalklyl and heteroaryl are intended to denote moieties wherein a heteroatoms is inserted into the carbon backbone of an alkyl or aryl structure (e.g., ether, thioether, and pyridinyl groups). Representative heteroatoms include N, O, S, Se, and Te. The terms alkyl, aryl, alkenyl, and alkynyl are intended to include moieties substituted with, for example, halogens or nitro, acid, or ester groups. Preferred alkyl and aryl groups have from 1 to about 10 carbon atoms and about 6 to about 14 carbon atoms, respectively. Preferred alkenyl and alkynyl groups have from 2 to about 10 carbon atoms. $R_C$, $R_D$, and $R_E$ preferably are alkyl, aryl, or trialkylsilyl.

$R_C$, $R_D$, and/or $R_E$ also can be chemical functional groups that include at least one peptide, nucleoside, and/or saccharide. For example, $R_C$, $R_D$, and $R_E$ can include a polymethylene chain connecting a DNA- or RNA-cleaving compound having formula (1) or (2) with an oligonucleotide. (see, e.g., Stein, et al., *Cancer Research* 1988, 48, 2659). As will be recognized, peptides are compounds comprising two or more amino acids covalently bound through an amide linkage (e.g., glycylalanine), nucleosides are glycosides comprising covalently bound pentoses and heterocyclic bases (e.g., cytidine), and saccharides are hemiacetal forms of polyhydroxy aldehydes and ketones (e.g., sucrose). Each of these terms is intended to include both naturally occurring and nonnaturally occurring moieties.

In preferred embodiments, each of $R_{A1}-R_{A4}$ is alkyl or aryl and either $R_{B5}$, $R_{B5}$ and $R_{B1}$, or $R_{B5}$ and $R_{B2}$ have formula $C=C(R_D)$. In other preferred embodiments, each of $R_{A1}-R_{A4}$ is alkyl or aryl and each of $R_{B1}-R_{B8}$ have formula $C=C(R_D)$. In still other preferred embodiments, $R_{A1}$ has formula $C=C(R_D)$, each of $R_{A2}-R_{A4}$ are alkyl or aryl, at least one of $R_{B1}-R_{B8}$ is H, alkyl or aryl, and $R_D$ is H, F, Cl, Br, I, alkyl, aryl, alkenyl, alkynyl, trialkylsilyl, or porphyrinato. In other preferred embodiments, $R_{A1}$ and $R_{A3}$ have formula $C=C(R_D)$, $R_{A2}$ and $R_{A4}$ are alkyl, aryl or a halogen, at least one of $R_{B1}-R_{B8}$ is H, alkyl, aryl or a halogen, and $R_D$ is H, F, Cl, Br, I, alkyl, aryl, alkenyl, alkynyl, trialkylsilyl, or porphyrinato; more preferably $R_D$ is 3,4,5-trialkyl-substituted phenyl or 3,4,5-trialkyloxy-substituted phenyl with the alkyl and alkoxy substituents having about 7 to about 20 carbon atoms. In still other preferred embodiments, $R_{A1}-R_{A4}$ have formula $C=C(R_D)$, at least one of $R_{B1}-R_{B8}$ is H, alkyl, aryl or a halogen, and $R_D$ is H, F, Cl, Br, I, alkyl, aryl, alkenyl, alkynyl, trialkylsilyl, or porphyrinato, more preferably $R_D$ is 3,4,5-trialkyl-substituted phenyl or 3,4,5-trialkoxy-substituted phenyl with the alkyl and alkoxy substituents having about 7 to about 20 carbon atoms.

The porphyrins of the invention are prepared by metal-mediated cross coupling of a halogenated, preferably brominated or chlorinated, porphyrin with an organometallic moiety. It is preferred that metallated porphyrins (e.g., formula (2)) be used; the cross-coupling product can be demetallated, if desired. The principles and techniques relating to metal-mediated cross coupling are well known to those skilled in the art to consist of three general steps: (1) oxidative addition, (2) transmetallation, and (3) reductive elimination. (See, e.g., Collman, et al., *Principles and Applications of Organotransition Metal Chemistry*, University Science Books, 1987, Mill Valley, CA; Kumada, *Pure & Appl. Chem.*, 1980, 52, 669; Hayashi, et al., *Tetrahedron Letter's*, 1979, 21, 1871.) In accordance with the invention, a halogenated porphyrin, $P_N-X_A$, is contacted with a catalyst having formula $Y(L)_2$ where Y is a metal such as, for example, Pd, Ni, Pt, Ru, or Cu and L is a ligand appropriate for that metal. When Y is Pd or Ni, L should be a phosphorous-, nitrogen- or arsenic-containing Lewis base such as an alkylphosphine or arylphosphine, a nitrogen-containing heterocycle such as pyridine, or a mixture thereof.

Contacting the halogenated porphyrin with the catalyst complex is believed to produce a second compound having formula $P_N-Y(L)_2X_A$, which is contacted with an organometallic compound having formula $T(R_L)_z(R_O)$, $T(R_L)_z(R_O)_t(X_B)_w$, $T(R_O)(X_B)$ or $T(R_O)_t$ where T is a metal such as, for example, Li, Na, K, Rb, Cs, Hg, Sn, Al, B, Si, Zn, Zr, Cd, Cu, or Mg; $X_B$ is a halogen or an alkoxy group; $R_L$ is cyclopentadienyl or aryl having about 6 to about 20 carbon atoms; $R_O$ is alkyl, alkenyl or alkynyl having 1 to about 10 carbon atoms, aryl having about 6 to about 20 carbon atoms such as $C(R_C)=C(R_D)(R_E)$, $C=C(R_D)$, haloalkyl groups or haloaryl groups; z and w are greater than or equal to 0; and t is at least 1. T can be any metal that does not participate in an outer sphere electron transfer reaction with the porphyrin. Representative organometallic compounds are $CUR_O$, $Zn(R_O)_2$, $ZnR_OX_B$, $(nBu)_3SnR_O$, and $Cp_2ZrR_OX_B$ (Cp=cyclopentadienyl). This contacting is believed to produce a third compound having formula $P_N-Y(L)_2R_O$ which, through reductive elimination, is transformed into substituted porphyrin $P_N-R_O$.

In general, the coupling reactions of the present invention proceed rapidly and in excellent yield, contrary to teaching in the prior art that reactions of this type should not work well with electron-rich systems such as porphyrins. It has been found that not all of the metals known for use in metal-mediated cross coupling reactions can be used to prepare substituted porphyrins. For example, coupling reactions wherein the metal T is lithium or magnesium have been found to proceed, if at all, in very low yield and with destruction of the porphyrin starting material.

The use of metal-mediated cross coupling in accordance with the invention can produce monomeric compounds suitable for incorporation into porphyrin-containing homopolymers or copolymers or into macromolecular or supramolecular species containing, for example, one or more peptides, nucleosides, or saccharides. The polymers according to the invention can contain as few as 2 porphyrin units, but more preferably contain at least 3 porphyrin units, more preferably at least 5 porphyrin units. In certain embodiments, polymers of the invention comprise a plurality of porphyrin units that, independently, have formula (1) or (2) wherein at least one of $R_{B1}-R_{B8}$ or $R_{A1}-R_{A4}$ includes a linking group selected from $[C(R_C)=C(R_D)(R_E)]_x$, $[C=C(R_D)]_x$, $[CH_2(R_C)-CH(R_D)(R_E)]_x$ or $[CH=CH(R_D)]_x$ where x is at least 1. Preferably, the remaining of $R_{A1}-R_{A4}$ are, independently, H, alkyl, alkenyl, alkynyl, or aryl and the remaining of $R_{B1}$-$R_{B8}$ are, independently, H, alkyl, aryl, $C(R_C)=C(R_D)(R_E)$, or $C=C(R_D)$.

In other embodiments, polymers according to the invention comprise a plurality of porphyrin units that, independently, have formula (1) or (2) wherein at least one of $R_{B1}$-$R_{B8}$ or $R_{A1}$-$R_{A4}$ is a cycloalkyl, cycloalkenyl, aryl or heteroaryl linking group having about 6 to about 22 carbon atoms.

Those skilled in the art will recognize the wide variety of polymers that can be prepared from the porphyrin-containing compounds of the invention. In certain embodiments, cofacial polymers are formed having, for example, formula (3).(see, e.g., Durand, et al., *J. Am. Chem. Soc.*, 1983, 105, 2710).

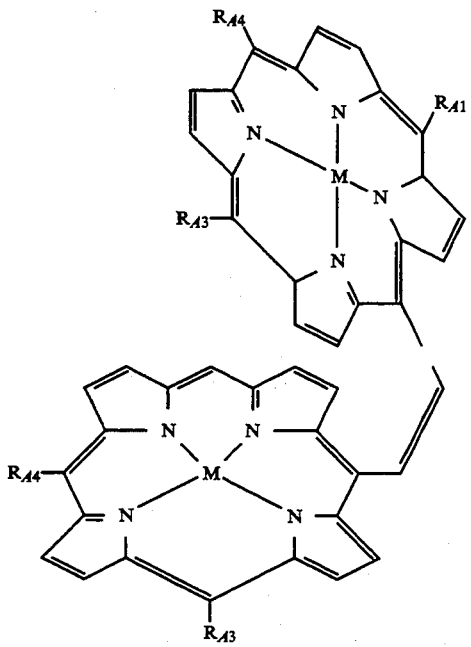

(3)

In other embodiments, somewhat linear polymer chains are formed wherein a portion of the polymer has general formula:

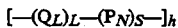

where $Q_L$ is a linking group, $P_N$ is a porphyrin unit, and h, l, and s are independently selected to be at least 1. For example, a portion of such polymers can have formula:

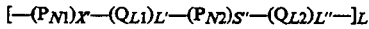

wherein $P_{N1}$ and $P_{N2}$ are independently selected porphyrin units, $Q_{L1}$ and $Q_{L2}$ are independently selected linking groups, and l', l'', s', and s'' are at least 1. These essentially linear polymer chains can be cross-linked such that a portion of the polymer has general formula:

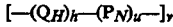

wherein $Q_H$ is a linking group, and h, u, and v are independently selected to be at least 1. A portion of these cross-linked polymers can have formula:

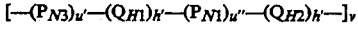

wherein $P_{N3}$ is a porphyrin unit, $Q_{H1}$ and $Q_{H2}$ are independently selected linking groups, and h', h'', u', and u'' are at least 1. Thus, one possible cross-linked polymer has formula:

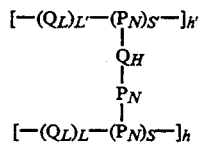

The polymers of the invention are generally formed by contacting a substituted porphyrin with a second compound containing functionality that is reactive with the functionality contained within the porphyrin. Preferably, the porphyrin contains an olefinic carbon-carbon double bond, a carbon-carbon triple bond or some other reactive functionality. The contacting should be performed under conditions effective to form a covalent bond between the respective reactive functionalities. Preferably, porphyrin-containing polymers are formed by metal-mediated cross-coupling of, for example, dibrominated porphyrin units. Also, porphyrin-containing polymers can be synthesized using known terminal alkyne coupling chemistry. (see, e.g., Patai, et al., The Chemistry of Functional Groups, Supplement C, Part 1, pp. 529-534, Wiley, 1983; Cadiot, et al., Acetylenes, pp. 597-647, Marcel Dekker, 1964; and Eglinton, et al., *Adv. Org. Chem.*, 1963, 4, 225) As will be recognized, the second compound noted above can be a substituted porphyrin of the invention or some other moiety such as an acrylate monomer. Thus, a wide variety of copolymeric structures can be synthesized with the porphyrins of the invention. Through careful substituent selection the porphyrins of the invention can be incorporated into virtually any polymeric matrix known in the art, including but not limited to polyacetylenes, polyacrylates, polyolefins, pohyethers, polyurethanes, polycarbonates, polyanilines, polypyrroles, and polythiophenes. For example, fluorescent porphyrins can be incorporated into such polymers as end-capping groups.

The porphyrins and porphyrin-containing polymers of the invention can be used, for example, as dyes, catalysts, contrast agents, antitumor agents, antiviral agents, liquid crystals, in chemical sensors and in electrooptical and solar energy conversion devices. They also can be incorporated into supramolecular structures. The polymers and supramolecular structures, which anchor porphyrin units in a relatively stable geometry, should improve many of the known uses for porphyrins and even provide a number of new uses, such as in a solid phase system for sterilizing virus-containing solutions. Representative uses are disclosed by, for example, the following patents, which are incorporated herein by reference: U.S. Pat. Nos. 4,895,682 (Ellis, et al.); 4,986,256 (Cohen); 4,668,670 (Rideout, et Ul.); 3,897,255 (Erickson); 3,899,334 (Erickson); 3,687,863 (Wacher); 4,647,478 (Formanek, et al.); and 4,957,615 (Ushizawa, et al.). Further uses are disclosed are disclosed by, for example, U.K. Patent Application 2,225,963 (Casson, et al.); International Application WO 89/11277 (Dixon, et al.); International Application WO 91/09631 (Matthews, et al.); European Patent Application 85105490.8 (Weishaupt, et al.); European Patent Application 90202953.7 (Terrell, et al.); European Patent Application 89304234.1 (Matsushima, et al.); Lehn, *Angew. Chem. Int. Ed. Engl.*, 1988, 27, 89; Wasielewski, *Chem. Rev.*, 1992, 92, 435; Mansury, et al., *J. Chem. Soc., Chem. Comm.*, 1985, 155; Groves, et al., *J. Am. Chem.*

Soc., 1983, 105, 5791; and Giroud-Godquin, et al., Angew. Chem. Int. Ed. Engl., 1991, 30, 375. It is believed that the porphyrins of the invention can be substituted for the porphyrins disclosed in each of the foregoing publications.

Additional objects, advantages, and novel features of this invention will become apparent to those skilled in the art upon examination of the following examples thereof, which are not intended to be limiting.

EXAMPLE 1

5,15-DIPHENYLPORPHYRIN

A flame-dried 1000 ml flask equipped with a magnetic stirring bar was charged with 2,2-dipyrrylmethane (458 mg, 3.1 mmol), benzaldehyde (315 μl, 3.1 mmol), and 600 ml of freshly distilled ($CaH_2$) methylene chloride. The solution was degassed with a stream of dry nitrogen for 10 minutes. Trifluoroacetic acid (150 μl, 1.95 mmol) was added via syringe, the flask was shielded from light with aluminum foil, and the solution was stirred for two hours at room temperature. The reaction was quenched by the addition of 2,3-dichloro-5,6-dicyano-1,4-benzoquinone (DDQ, 900 mg, 3.96 mmol) and the reaction was stirred for an additional 30 minutes. The reaction mixture was neutralized with 3 ml of triethylamine and poured directly onto a silica gel column (20 ×2 cm) packed im hexane. The product was eluted in 700 ml of solvent. The solvent was evaporated, leaving purple crystals (518 mg., 1.12 mmol, 72.2%). This product was sufficiently pure for further reactions. Vis($CHCl_3$): 421 (5.55), 489 (3.63), 521 (4.20), 556 (4.04), 601 (3.71), 658 (3.73).

EXAMPLE 2

5,15-DIBROMO-10,20-DIPHENYLPORPHYRIN 5,15-Diphenylporphyrin (518 mg, 1.12 mmol) was dissolved in 250 ml of chloroform and cooled to 0° C. Pyridine (0.5 ml) was added to act as an acid scavenger. N-Bromosuccinimide (400 mg, 2.2 mmol) was added directly to the flask and the mixture was followed by TLC (50% $CH_2Cl_2$/hexanes eluant). After 10 minutes the reaction reached completion and was quenched with 20 ml of acetone. The solvents were evaporated and the product was washed with several portions of methanol and pumped dry to yield 587 mg (0.94 mmol, 85%) of reddish-purple solid. The compound was sufficiently pure to use in the next reaction. Vis($CHCl_3$): 421 (5.55), 489 (3.63), 521 (4.20), 556 (4.04), 601 (3.71), 658 (3.73).

EXAMPLE 3

5,15-DIBROMO-10,20-DIPHENYLPORPHYRINATO ZINC 5,15-Dibromo-10,20-diphenylporphyrin (587 mg, 0.94 mmol) was suspended in 30 ml DMF containing 500 mg $ZnCl_2$. The mixture was heated at reflux for 2 hours and poured into distilled water. The precipitated purple solid was filtered through a fine fritted disk and washed with water, methanol, and acetone and dried in vacuo to yield 610 mg (0.89 mmol, 95%) of reddish purple solid. The compound was recrystallized from THF/heptane to yield large purple crystals of the title compound (564 mg, 0.82 mmol, 88%). Vis(THF): 428 (5.50), 526 (3.53), 541 (3.66), 564 (4.17), 606 (3.95).

EXAMPLE 4

MESO-SUBSTITUTED PORPHYRINS

General Procedure

In each of the following examples, 5,15-Dibromo-10,20-diphenylporphyrinato zinc (0.1 mmol), and Pd($PPh_3$)$_4$ (0.0025 mmol) were dissolved in 35 ml of distilled, degassed THF in a sealed storage tube with the 1 mmol of the indicated organometallic reagent and warmed at 60° C. for 48 hours. The reaction was monitored by TLC on withdrawn aliquots. The mixture was quenched with water, extracted with chloroform, dried over $CaCl_2$, evaporated and purified by column chromatography.

A. 5,15-Diphenyl-10,20-dimethylporphyrinato zinc

The organometallic reagent was methyl zinc chloride prepared from methyl lithium and anhydrous zinc chloride in THF.

The crude solid was dissolved in THF/heptane, poured onto 10 g silica gel and evaporated to dryness. This silica gel was loaded onto a column packed in 50% $CH_2Cl_2$/hexane. A single band was eluted (50% $CH_2Cl_2$/hexane) to yield pure 5,15-diphenyl-10,20-dimethylporphyrinato zinc (48 mg, 88%). An analytical sample was recrystallized from THF/heptane by slow evaporation under $N_2$. $^1$H NMR (500 MHz, 3:1 $CDCl_3$, $D_8$-THF) ε9.34 (d, 4H, J=4.6); 8.71 (d, 4H, J=4.6); 8.02 (dd, 4H, $J_1$=7.5, $J_2$=1.4); 7.57 (m, 6H); 4.51 (s, 6H). $^{13}$C NMR (125 MHz, 3:1 $CDCl_3$, $D_8$-THF) ε150.07 (0), 148.88 (0), 143.34 (0), 134.18 (1), 131.42(1), 128.09(1), 126.73(1), 125.88(1), 119.29(0), 113.74(0), 20.81(3). Vis (THF) 424 (5.58), 522 (3.40), 559 (4.12); 605 (3.88).

B. 5,15-Diphenyl-10,20-divinylporphyrinato zinc

The organometallic reagent was tri-n-butylvinyl tin.

The crude product was absorbed on silica and loaded onto a column packed in hexane. Elution was carried out with $CH_2Cl_2$(0–50%)/hexane. A small quantity of purple material led the main fraction. The main band was evaporated to yield pure 5,15-diphenyl-10,20-divinylporphyrinato zinc (53 mg, 91%). An analytical sample was recrystallized from chloroform. $^1$H NMR (500 MHz, $CDCl_3$) ε9.52 (d, 4H, J=4.7); 9.24(dd, 2H, $J_1$=17.3, $J_2$=9.1); 8.92 (d, 4H, J=4.7); 8.19 (dd, 4H, $J_1$=6.8, $J_2$=2.0); 7.75 (m, 6H); 6.48 (dd, 2H, $J_1$=11.0, $J_2$=1.9); 6.05 (dd, 2H, $J_1$=17.3, $J_2$=2.0). $^{13}$C NMR (125 MHz, $CDCl_3$) ε163.40(1), 149.90(0), 149.21(0), 142.83(0), 137.97(0), 134.40(1), 132.10(1), 130.39(1), 127.50(1), 126.73(2), 126.57(1), 121.05(0).

C. 5,15-Bis(2,5-dimethoxyphenyl)-10,20-diphenylporphyrinato zinc

The organometallic reagent was 2,5-dimethoxyphenyl lithium, prepared from 1,4-dimethoxybenzene and t-butyl lithium in ether at −78° C. The organolithium reagent was added to a solution of $ZnCl_2$ in THF to yield the organozinc chloride reagent. This reagent was used immediately.

At the completion of the reaction two highly fluorescent spots were visible by TLC. The crude product was chromatographed on silica using $CHCl_3$ as eluant. The first band off the column proved to be the $C_{2h}$ isomer of 5,15-bis(2,5-dimethoxyphenyl)-10,20-diphenylporphyrinato zinc. This band was evaporated leaving 33 mg (42%) of pure product. An analytical sample was recrystallized from chloroform. $^1$H NMR (500 MHz,CDCl$_3$) ε8.91 (s, 8H); 8.22 (d, 4H, J=6.5); 7.75 (m, 6H); 7.59 (d, 2H, J=2.2); 7.26 (broad s, 4H); 3.86 (s, H); 3.54 (s, 6H). $^{13}$C NMR (125 MHz, CDCl$_3$) ε154.10(0), 152.30(0), 150.13(0), 143.00(0), 134.10(1), 132.62(0), 132.00(1), 131.44(1), 127.35(1), 126.44(1), 121.34(1), 120.69(0), 110.59(0), 114.76(1), 112.31(1), 56.70(3), 55.95(3). Vis—424 (5.64), 551 (4.34), 584 (3.43).

The C$_{2v}$ isomer followed the C$_{2h}$ isomer off the column. The solvent was evaporated leaving 30 mg (32%) of pures, 15-bis(2,5-dimethoxyphenyl)-10,20-diphenylporphyrinato zinc. This compound is much more soluble in chloroform than the C$_{2h}$ isomer. The assignment of stereochemistry was made from the NMR data. $^1$H NMR (500 MHz,CDCl$_3$) ε8.90 (s, 8H); 8.21 (d, 2H, J=7.9); 8.19 (d, 2H, J=6.5); 7.73 (m, 6H); 7.58 (s, 2H); 7.24 (broad s, 4H); 3.84 (s, 6H); 3.53 (s, 6H). $^{13}$C NMR (125 MHz CDCl$_3$) ε154.14 (0); 152.31 (0), 150.15 (0), 142.94(0), 134.40(1), 132.66(0), 132.02(1), 131.48(1), 127.37(1), 126.46(1), 126.44(1), 121.30(1), 120.72(0), 116.69(0), 114.73(1), 112.28(1), 56.75(3), 55.92(3).

D. 5,15-Bis[(4-methyl)-4'-methyl-2,2'-dipyridyl)]-10,20-diphenylporphyrinato zinc The organometallic reagent was tri-n-butyl[(4-methyl)-4'-methyl-2,2'-dipyridyl)]tin, prepared by lithiating 4,4'-dimethyl-2,2'-dipyridyl with one equivalent of lithium diisopropylamide in THF at −78° C. and warming the reaction mixture to room temperature. The organolithium reagent was treated with 1.1 equivalent of tributyltin chloride. The resulting organotin reagent was used without further purification.

Chromatography of the crude reaction mixture was carried out on silica with a mixture of CH$_2$Cl$_2$, isopropanol, and triethylamine. The porphyrin was eluted in one broad band. The product obtained from this procedure (68% yield) was contaminated with a small amount (0.2 eq per eq of porphyrin) of triphenylphosphine. $^1$H NMR (500 MHz, CDCl$_3$) ε9.37 (d, 4H, J=4.7); 8.87 (d, 4H, J=4.7); 8.52 (s, 2H); 8.29 (d, 2H, J=5.1); 8.20 (d, 2H, J=5.2); 8.10 (m, 6H); 7.71 (m, 6H); 7.01 (d, 2H, J=5.0); 6.88 (d, 2H, J=4.2); 6.46 (s, 4H); 2.32 (s, 6H).

E. 5,15-Bis(trimethylsilylethynyl)-10,20-diphenylporphyrinato zinc

The organometallic reagent was trimethylsilyl ethynyl zinc chloride prepared from trimethylsilylethynyl lithium and anhydrous zinc chloride in THF.

After 48 hours the reaction was bright green. The crude solid was absorbed on silica gel, loaded onto a column packed in hexane, and chromatographed with 20%–30% CH$_2$Cl$_2$/hexane. Clean separation of the product from the small quantities of deprotected products were obtained by this method. The solvents were evaporated and the purple solid was washed twice with hexane and dried in vacuo. $^1$H NMR (500 MHz, CDCl$_3$) ε9.68 (d, 4H, J=4.6); 8.89 (d, 4H, J=4.6); 8.15 (dd, H, J$_1$=7.9, J$_2$=1.7); 7.75 (m, 6H); 0.58 (s, 18H). $^{13}$C NMR (125 MHz, CDCl$_3$) ε152.22, 150.26, 142.10, 134.39, 132.77, 131.29, 27.69, 126,67, 115.08, 107.34, 102.00, 0.32.

EXAMPLE 5
PYRROLE-SUBSTITUTED PORPHYRINS

General Procedure

2-Bromo-5,10,15,20-tetraphenylporphyrinato zinc (0.1 retool) and palladium 1,1'-bis (diphenylphosphino) ferrocene) dichloride (Pd(dppf)Cl$_2$, 7 mg) were combined with 1.0 mmol of the organometal lic reagent indicated below in 35 ml dry, degassed THF. The solution was allowed to stand for 12 hours, the solvent evaporated, and the compound purified by flash chromatography.

A. 2-Vinyl-5,10,15,20-tetraphenyl porphyrinato zinc

The organometalic reagent was tributylvinyl tin.

The crude reaction mixture was chromatographed on silica and eluted with 50% CH$_2$Cl$_2$/hexane. $^1$H NMR (250 MHz, CDCl$_3$) ε8.97 (s, 1H); 8.90 (m, 4H); 8.87 (d, 1H, J=4.7); 8.79 (d, 1H, J=4.7); 8.20 (m, 6H); 8.06 (d, 2H, J=6.6); 7.74 (m, 12H); 6.39 (dd, 1H, J$_1$=17.0, J$_2$=9.1); 5.83 (dd, 1H, J$_1$=17.1, J$_2$=2.0); 5.01 (dd, 1H, J$_1$=10.7, J$_2$=2.0). Vis (CHCl$_3$) 426 (5.53), 517 (3.68); 555 (4.22), 595 (3.68).

B. 2-(2,5-dimethoxyphenyl)-5,10,15,20-tetraphenyl porphyrinato zinc

The organometallic reagent was 2,5-dimethoxyphenyl zinc chloride, prepared from the corresponding lithium reagent and anhydrous zinc chloride in THF/diethyl ether.

Flash chromatograph of the crude reaction mixture was carried out with chloroform. The title compound was isolated in 78% yield. $^1$H NMR (500 MHz, CDCl$_3$) ε=8.94 (d, 1H, J=4.7); 8.93 (s,2H); 8.92 (d, 1H, J=4.8); 8.85 (s, 1H); 8.84 (d, 1H, J=4.7); 8.70 (d, 1H, J=4.7); 8.23 (m, 6H); 7.98 (d, 1H, J=7.0); 7.70 (m, 10H); 7.25 (quintet, 2H, J=7.4); 7.15 (t, 1H, J=7.0); 6.92 (d, 2H, J=3.1); 6.54 (dd, 1H, J$_1$=9.0, J$_2$=3.2); 6.40 (d, 1H, J=9.1); 3.68 (s, 3H); 3.42 (s, 3H). $^{13}$C NMR (125 MHz, CDCl$_3$) ε=152.59(0), 151.33(0), 150.46(0), 150.31(0), 150.27(0), 150.15(0), 150.12(0), 150.03(0), 148.30(0), 147.16(0), 143.32(0), 142.97(0), 142.86,140.71(0), 135.63(1), 135.20(1), 134.45(1), 134.13(1), 132.52(1), 132.02(1), 131.91(1), 131.82(1), 131.32(1), 129.27(0), 127.44(1), 127.38(1), 127.18(1), 126.53(1), 126.50(1), 124.91(1), 121.70(1), 122.36(0), 121.30(0), 120.91(0), 120.54(0), 113.15(1), 113.03(1), 110.35(1), 55.98(3), 54.87(3). Vis (CHCl$_3$) 421.40(5.60), 513.2 (3.45), 549.75 (4.28), 587.15 (3.45).

C. 2-(Trimethylsilylethynyl)-5,10,15,20-tetraphenyl porphyrinato zinc

The organometallic reagent, trimethylsilylacetylide zinc chloride, was prepared from the corresponding lithium reagent and anhydrous zinc chloride in THF.

The crude reaction mixture was chromatographed on silica and eluted with 50% CH$_2$Cl$_2$/hexane. $^1$H NMR (250 MHz, CDCl$_3$) ε9.25 (s, 1H); 8.89 (m, 4H); 8.85 (d, 1H, J=4.9); 8.76 (d, 1H, J=4.9); 8.16 (m, 6H); 8.09 (d, 2H, J=7.1); 7.67 (m, 12H); 0.21 (s, 9H). Vis (CHCl$_3$) 431 (5.43), 523 (shoulder); (4.18), 598 (3.67).

D. 2-n-butyl-5,10,15,20-tetraphenyl porphyrinato zinc

Butyl zinc chloride was prepared from n-butyllithium and anhydrous zinc chloride in THF.

The crude reaction mixture was chromatographed on silica and eluted with 50% CH$_2$Cl$_2$/hexane. $^1$H NMR (250 MHz, CDCl$_3$) ε8.97 (m, 4H); 8.91 (d, 1H, J=4.7); 8.77 (d, 1H, J=4.7); 8.74 (s, 1H); 8.22 (m, 6H); 8.13 (d, 2H, J=7.3); 7.77 (m, 12H); 2.81 (t, 2H, J=7.7); 1.83

(quint, 2H, J=7.8); 1.30 (quint, 2H, J=7.6); 0.91 (t, 3H, J=8.2).

EXAMPLE 6

VINYLIC-BRIDGED PORPHYRINS AND THEIR POLYMERS

A. cis-Bis-1,2-[5-(10,15,20-triphenylporphyrinato) zinc]ethene

5-Bromo-10,15,20-triphenylporphyrinato zinc (0.2 mmol) and Pd(PPh$_3$)$_4$ (0.02 mmole) are dissolved in 25 ml dry, degassed THF. A solution of cis-bis(tri-n-butyltin)ethene (0.2 mmol) in 5 ml THF is added and the solution heated at reflux for 2 days. The reaction is quenched with water, extracted with methylene chloride, dried over calcium chloride, and the solvents are evaporated. The crude solid is chromatographed on silica using methylene chloride/hexane eluant to isolate a dimer having formula (3), wherein R$_{A1}$, R$_{A3}$, and R$_{A4}$ are phenyl and M is Zn.

B. cis-Bis-1,2-{5-[10,15,20-tris(pentafluoro-phenyl)]-2,3,7,8,12,13,17,18-octakis-(trifluoromethyl) porphyrinato zinc}-1,2-difluoroethene 5-Bromo-10,15,20-tris(pentafluorophenyl)porphyrinato zinc (0.2 mmol) and Pd(PPh$_3$)$_4$ (0.02 mmol) are dissolved in 25 ml dry THF. A solution of cis-bis(tri-n-butyltin)-1,2-difluoroethene (0.2 mmol) in 5 ml THF is added and the solution heated at reflux for 2 days. The reaction is quenched with water, extracted with methylene chloride, dried over calcium chloride, and the solvents evaporated. The crude solid is chromatographed on silica using methylene chloride/hexanes eluent to isolate cis-bis-1,2-{5-[10,15,20-tris(pentafluorophenyl)porphyrinato zinc}-1,2-difluoroethene.

This material is dissolved in chloroform and reacted with a large excess of N-bromosuccinimide as in Example 2 to perbrominate positions R$_{B1}$–R$_{B8}$ on both porphyrins. The resulting material filtered through a fine fritted disk and washed with water, methanol, and acetone, dried in vacuo, and then recrystallized from THF/heptane. cis-Bis-1,2-{5-[10,15,20-tris(pentafluorophenyl)-2,3,7,8,12,13,17,18-octabromoporphyrinato zinc is reacted with Pd(dppf) and a large excess of CuCF$_3$ in the dark as in Example 4. After a reaction time of about 48 hours, the product is chromatographed on silica with CH$_2$Cl$_2$/CCl$_4$ eluent to yield the title compound.

C. Cofacial-bis-[cis-ethenyl meso-bridged]porphyrin[CEBP](Formula (4)) and Polymeric-bis-[cis-ethenyl meso-bridged]porphyrin [PABP](Formula (5))

5,15-Dibromo-10,20-diphenylporphyrinato zinc (0.2 mmol) and Pd(PPh$_3$)$_4$ (0.02 mmole) are dissolved in 25 ml dry, degassed THF. A solution of cis-bis(tri-n-butyltin)ethene (0.2 mmol) in 5 ml THF is added and the solution heated at reflux for 2 days. The reaction is quenched with water, extracted with methylene chloride, dried over calcium chloride, and the solvents are evaporated. The crude solid is chromatographed on silica using methylene chloride/hexane eluant to isolate the Cofacial-bis-[cis-ethenyl meso-bridged]zinc porphyrin complex of formula (4) and Polymeric-bis-[cisethenyl meso-bridged] porphyrin species of formula (5), wherein R$_{A1}$ and R$_{A3}$ are phenyl and M is Zn.

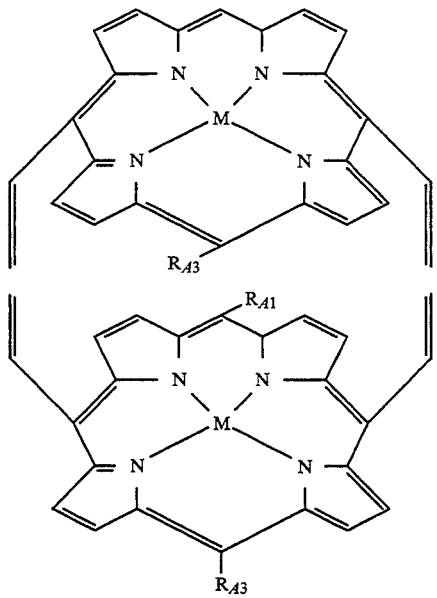

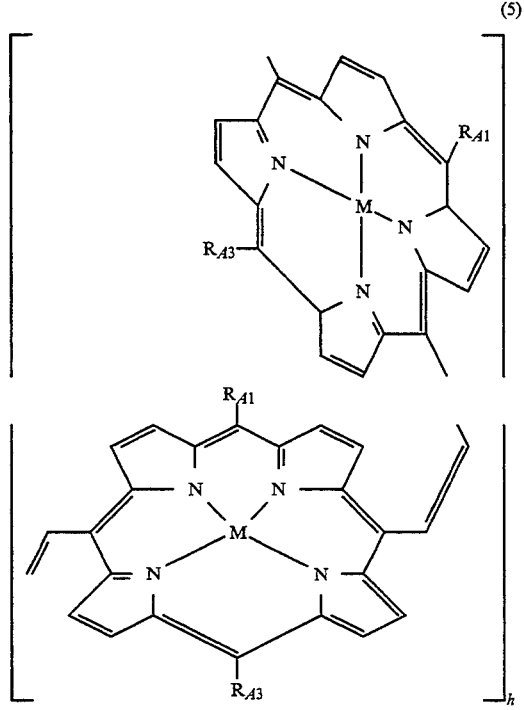

D. Fluorinated Cofacial-bis-[cis-ethenyl mesobridged]porphyrin[FCEBP]and Fluorinated Polymeric-bis-[cis-ethenyl meso-bridged]porphyrin [FPEBP]

5,15-Dibromo-10,20-bis(pentafluorophenyl) porphyrinato zinc (0.2 mmol) and Pd(PPh$_3$)$_4$ (0.02 mmol) are dissolved in 25 ml dry THF. A solution of cis-bis(tri-n-butyltin)-1,2-difluoroethene (0.02 mmol) in 5 ml THF is added and the solution heated at reflux for 2 days. The reaction is quenched with water, extracted with methylene chloride, dried over calcium chloride, and the solvents evaporated. The crude solid is chromatographed on silica using methylene chloride/hexanes eluent to isolate the Cofacial-bis-[cisethenyl mesobridged] zinc porphyrin complex as well as the Polymeric-bis-[cis-ethenyl meso-bridged] porphyrin species. The cofacial and polymeric species are dissolved separately in chloroform. The cofacial porphyrin complex dissolved in chloroform and reacted with a large excess of N-bromosuccinimide as in Example 2 to perbrominate positions $R_{B1}$–$R_{B8}$ on both porphyrins. The resulting material filtered through a fine fritted disk and washed with water, methanol, and acetone, dried in vacuo, and then recrystallized from THF/heptane to yield the title compound. The isolated material is reacted with Pd(dppf) and a large excess of $CuCF_3$ in the dark in a manner as in Example 4. After a reaction time of about 48 hours, the product is chromatographed on silica with $CH_2Cl_2/CCl_4$ eluent to yield a perfluorinated CEPB analogous to formula (4). Perfluorinated PEBP is synthesized in a similar manner, yielding a species analogous to formula (5) where highly fluorinated porphyrins are linked via fluorovinyl units.

E. Cofacial-bis-[1,8-anthracenyl-meso-bridged]porphyrin [CBAP] (Formula (6)) and Polymeric-bis-[1,8-anthracenyl-meso-bridged][PBAP]porphyrin (Formula (7))

5,15-Dibromoporphyrinato zinc (0.2 mmol) and $Pd(PPh_3)_4$ (0.02 mmol) are dissolved in 25 ml dry, degassed THF. A solution of 1,8-anthracenyl-bis-(tributyl tin) (0.2 mmol) in 5 ml THF is added and the solution heated at reflux for 2 days. The reaction is quenched with water, extracted with methylene chloride, dried over calcium chloride, and the solvents are evaporated. The crude solid is chromatographed on silica using methylene chloride/hexane eluant to isolate the Cofacial-bis-[1,8-anthracenyl-meso-bridged]zinc porphyrin complex of formula (6) and the Polymeric-bis-[1,8-anthracenyl-meso-bridged]zinc porphyrin species of formula (7), where and $R_{A3}$ are phenyl and M is Zn.

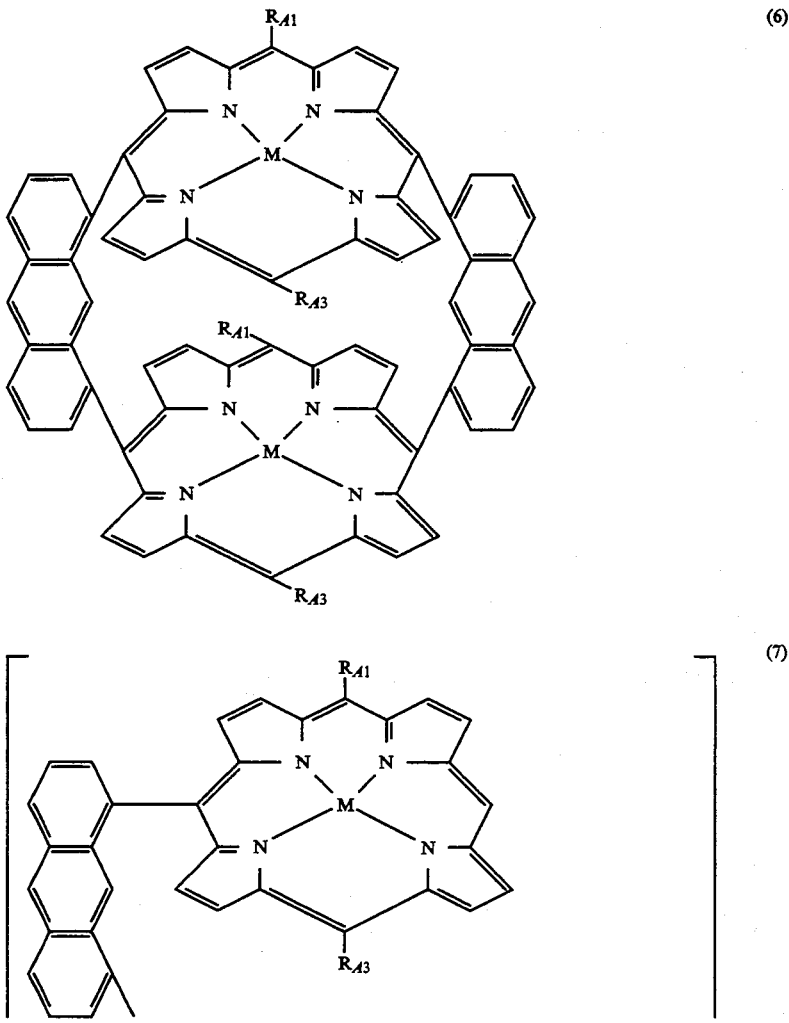

-continued

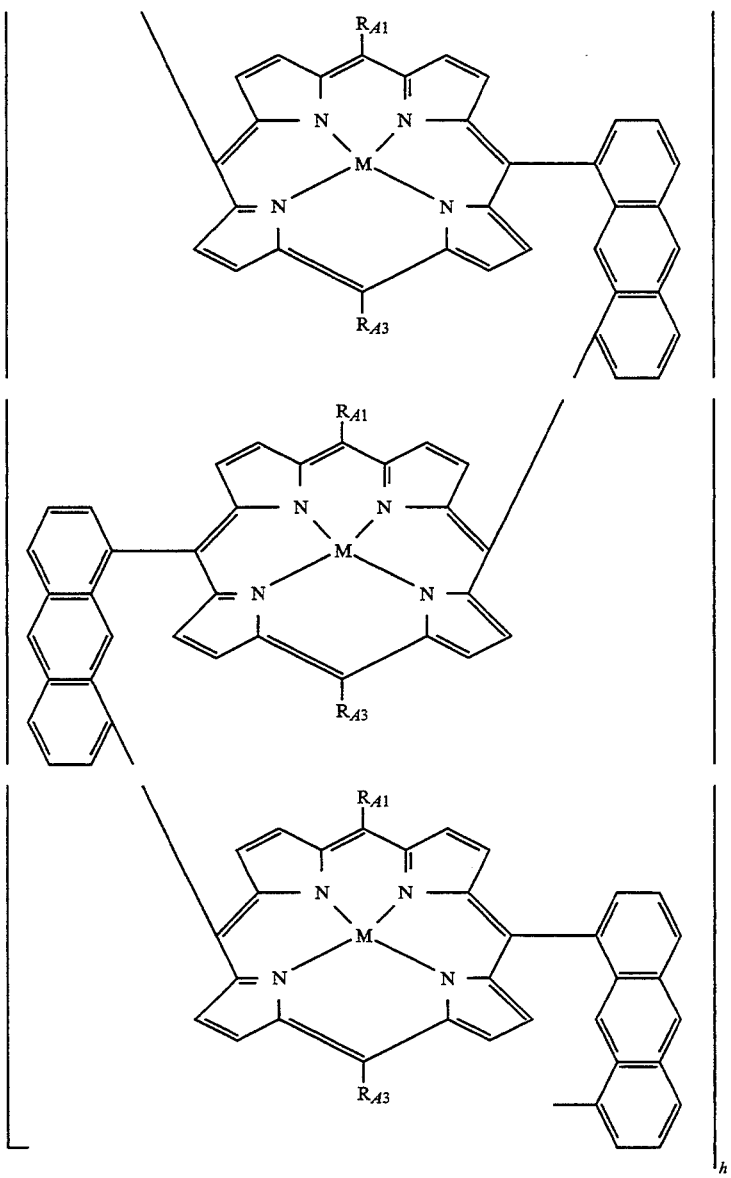

EXAMPLE 7
ACETYLENIC PORPHYRIN POLYMERS

A. Poly(5,15-bis(ethynyl)-10,20-diphenylporphyrinato zinc)

5,15-Bis(ethynyl)-10,20-diphenylporphyrinato zinc (0.2 mmol) in pyridin (20 ml) is slowly added to a solution of cuptic acetate (0.4 mmol) in 20 ml 1:1 pyridine/methanol generally according to the procedure of Eglinton, et al., The Coupling of Acetylenic Compounds, p. 311 in Advances in Organic Chemistry, Raphael, et al., eds., 1963, Interscience Publishers.

B. Poly(5,15-bis(ethynylphenyl)-10,20-diphenylporphyrinato zinc)

5,15-Diethynyl-10,20-diphenylporphinato zinc (0.2 mmol) and 1,4-dibromobenzene are combined in a mixture of 30 ml toluene and 10 ml di/sopropylamine. CuI (0.4 mmol) and Pd(Ph$_3$)$_4$ (0.02 mmol) are added and the mixture is heated at 65° C. for 3 days. The crude solid is washed with methanol and acetone and dried in vacuo.

Alternatively, the polymer is prepared from 1,4-diethynylbenzene and 5,15-dibromo-10,20-diphenylporphinato zinc via the identical procedure.

EXAMPLE 8
DOPED PORPHYRIN POLYMERS 5,15-Bis(ethynyl)-10,20-diphenylporphyrinato zinc is polymerized according to the generally procedure provided by Skotheim, ed., Handbook of Conducting Polymers, Volume 1, pp. 405–437, Marcel Dekker, 1986 using a catalytic amount of MoCl$_5$, Me(CO)$_6$, WCl$_6$, or W(CO)$_5$. The resultant polymer is then doped with an oxidant such as iodine or SbF$_5$.

Those skilled in the art will appreciate that numerous changes and modifications may be made to the preferred embodiments of the invention and that such changes and modifications may be made without departing from the spirit of the invention. For example, it is believed that the methods of the present invention can be practiced using porphyrin-related compounds such as chiefins, phorbins, bacteriochlorins, porphyrinogens, sapphyrins, texaphrins, and pthalocyanines in place of porphyrins. It is therefore intended that the appended claims cover all such equivalent variations as fall within the true spirit and scope of the invention.

What is claimed is:

1. A compound having formula (1) or (2):

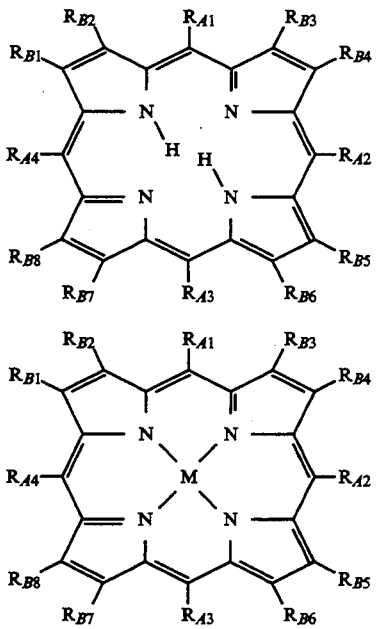

wherein:
(a) at least two of $R_{A1}-R_{A4}$ has formula $CH=CH_2$; or
(b) at least one of $R_{B1}-R_{B8}$ has formula $C(R_C)=C(R_D)(R_E)$, provided that at least one of $R_C$, $R_D$, and $R_E$ is not H; or
(c) at least two of $R_{B1}-R_{B8}$ have formula $C=C(R_D)$; or
(d) at least one of $R_{A1}-R_{A4}$ is haloalkyl having 1 to about 20 carbon atoms; or
(e) at least one of $R_{B1}-R_{B8}$ is haloalkyl having 2 to about 20 carbon atoms; or
(f) at least five of $R_{B1}-R_{B8}$ are haloalkyl having 1 to about 20 carbon atoms or haloaryl having about 6 to about 20 carbon atoms; or
(h) at least one of $R_{A1}-R_{A4}$ has formula $C(R_C)=C(R_D)(R_E)$, provided that at least two of $R_C$, $R_D$ and $R_E$ are not H; or
(i) at least two of $R_{A1}-R_{A4}$ have formula $C(R_C)=C(R_D)(R_E)$, provided that at least one of $R_C$, $R_D$, and $R_E$ is not H;

where $R_C$, $R_D$, and $R_E$ are, independently, H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinatol; and M is a chelated metal atom.

2. The compound of claim 1 wherein at least two of $R_{A1}-R_{A4}$ has formula $CH=CH_2$.

3. The compound of claim 1 wherein at least one of $R_{B1}-R_{B8}$ has formula $C(R_C)=C(R_D)(R_E)$, provided that at least one of $R_C$, $R_D$, and $R_E$ is not H.

4. The compound of claim 1 wherein at least two of $R_{B1}-R_{B8}$ have formula $C=C(R_D)$.

5. The compound of claim 1 wherein at least one of $R_{A1}-R_{A4}$ is haloalkyl having 1 to about 20 carbon atoms.

6. The compound of claim 1 wherein at least one of $R_{B1}-R_{B8}$ is haloalkyl having 2 to about 20 carbon atoms.

7. The compound of claim 1 wherein at least five of $R_{B1}-R_{B8}$ are haloalkyl having from 1 to about 20 carbon atoms.

8. The compound of claim 1 wherein at least one of $R_{B1}-R_{B8}$ is haloaryl having about 6 to about 20 carbon atoms.

9. The compound of claim 1 wherein at least one of $R_{B1}-R_{B8}$ is haloaryl having about 6 to about 20 carbon atoms.

10. The compound of claim 1 wherein at least one of $R_{B1}-R_{B8}$ is alkyl having 1 to about 20 carbon atoms or aryl having 6 to about 20 carbon atoms.

11. The compound of claim 10 wherein $R_{B5}$ has formula $C=C(R_D)$ and each of $R_{A1}-R_{A4}$ are alkyl having 1 to about 20 carbon atoms or aryl having 6 to about 20 carbon atoms.

12. The compound of claim 10 wherein $R_{B1}$ and $R_{B5}$ have formula $C=C(R_D)$ and each of $R_{A1}-R_{A4}$ are alkyl having 1 to about 20 carbon atoms or aryl having 6 to about 20 carbon atoms.

13. The compound of claim 10 wherein $R_{B2}$ and $R_{B5}$ have formula $C=C(R_D)$ and each of $R_{A1}-R_{A4}$ are alkyl having 1 to about 20 carbon atoms or aryl having 6 to about 20 carbon atoms.

14. The compound of claim 10 wherein each of $R_{B1}-R_{B8}$ have formula $C=C(R_D)$ and each of $R_{A1}-R_{A4}$ are alkyl having 1 to about 20 carbon atoms or aryl having 6 to about 20 carbon atoms.

15. The compound of claim 10 wherein at least one of $R_{B1}-R_{B8}$ is H, alkyl having 1 to about 20 carbon atoms, aryl having 6 to about 20 carbon atoms, F, Cl, Br, or I.

16. The compound of claim 15 wherein $R_{A1}$ has formula $C=C(R_D)$, each of $R_{A2}-R_{A4}$ are alkyl having 1 to about 20 carbon atoms, aryl having 6 to about 20 carbon atoms, F, Cl, Br, or I, and $R_D$ is H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinato.

17. The compound of claim 15 wherein $R_{A1}$ and $R_{A3}$ have formula $C=C(R_D)$, $R_{A2}$ and $R_{A4}$ are alkyl having 1 to about 20 carbon atoms, aryl having 6 to about 20 carbon atoms, F, Cl, Br, or I, and $R_D$ is H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, triaikylsilyl, or porphyrinato.

18. The compound of claim 17 wherein $R_D$ is 3,4,5-trialkyl-substituted phenyl or 3,4,5-trialkyloxy-substituted phenyl wherein said alkyl and alkoxy substituents have about 7 to about 20 carbon atoms.

19. The compound of claim 15 wherein $R_{A1}-R_{A4}$ have formula $C=C(R_D)$ and $R_D$ is H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinato.

20. The compound of claim 19 wherein $R_D$ is 3,4,5-trialkyl-substituted phenyl or 3,4,5-trialkyloxy-substituted phenyl wherein said alkyl and alkoxy substituents have about 7 to about 20 carbon atoms.

21. The compound of claim 1 wherein M is a lanthanide or actinide or Sc, Ti, V, Cr, Mn, Fe, Co, Ni, Cu, Y, Zr, Nb, Mo, Ru, Rh, Pd, Ag, La, Hf, Ta, W, Re, Os, Ir, Pt, Cd, Hg, Li or Au.

22. The compound of claim 1 wherein M is a metal having a full valence shell.

23. The compound of claim 1 wherein M is Zn or Mg.

24. A compound having formula (1) or (2):

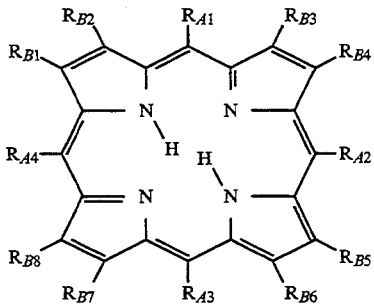
(1)

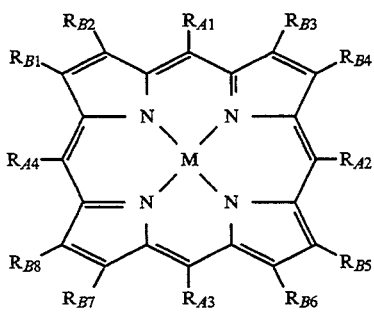
(2)

wherein:
at least one of $R_{A1}-R_{A4}$ or $R_{B1}-R_{B8}$ is a halogen; and
at least one of the remaining $R_{A1}-R_{A4}$ or $R_{B1}-R_{B8}$ is $C(R_C)=C(R_D)(R_E)$, $C\equiv C(R_D)$, haloalkyl having from 1 to about 20 carbon atoms, or haloaryl having about 6 to about 20 carbon atoms where $R_C$, $R_D$, and $R_E$ are, independently, H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinato; and M is a chelated metal atom.

25. A compound having formula (1) or (2):

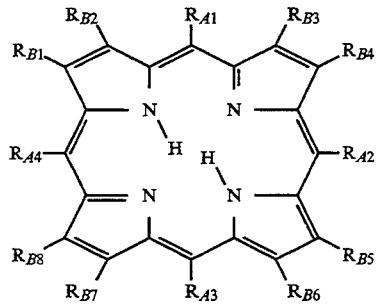
(1)

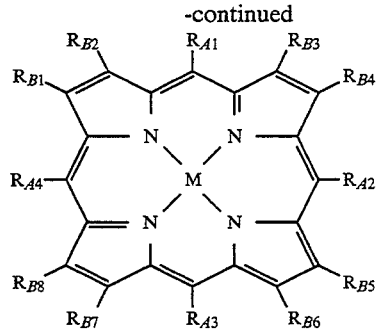
(2)

wherein M is a chelated metal atom and at least one of $R_{A1}-R_{A4}$ or $R_{B1}-R_{B8}$ has formula $Y(L)_2X_A$ where Y is a metal, L is a ligand, and $X_A$ is a halogen.

26. A compound having formula (1) or (2):

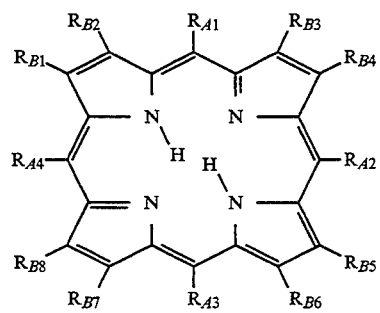
(1)

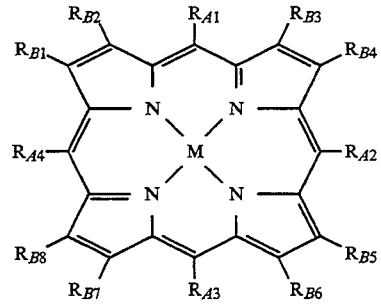
(2)

wherein at least one of $R_{A1}-R_{A4}$ or $R_{B1}-R_{B8}$ has formula $Y(L)_2R_O$ where M is a chelated metal atom, Y is a metal; L is a ligand; and $R_O$ is alkyl having 1 to about 10 carbon atoms, alkenyl or alkynyl having 2 to about 10 carbon atoms, aryl having bout 6 to about 20 carbon atoms.

27. The compound of claim 1 wherein at least one of $R_{A2}$ and $R_{A4}$ are halogen.

28. A compound having formula (1) or (2):

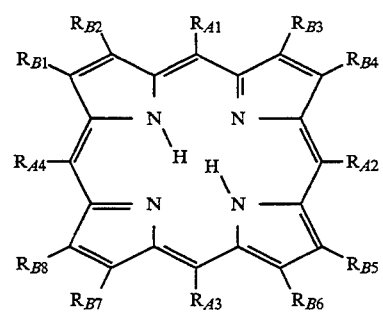
(1)

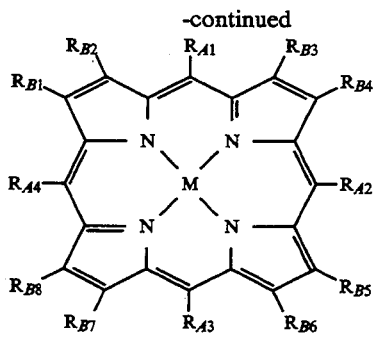

wherein:
(a) $R_{A1}$ has formula $C=C(R_D)$ provided that $R_D$ is not H or alkyl having 1 to about 20 carbon atoms; or
(b) $R_{A1}$ and $R_{A2}$ have formula $C=C(R_D)$; or
(c) $R_{A1}$ and $R_{A3}$ have formula $C=C(R_D)$ and $R_{A2}$ and $R_{A4}$ are not H; or
(d) $R_{A1}$, $R_{A2}$, and $R_{A3}$ have formula $C=C(R_D)$; or
(e) $R_{A1}$-$R_{A4}$ have formula $C=C(R_D)$ provided that $R_{B1}$-$R_{B8}$ are not H or alkyl having 1 to about 20 carbon atoms; or
(f) $R_{A1}$-$R_{A4}$ have formula $C=C(R_D)$ provided that $R_D$ is not H or trialkylsilyl;

where $R_D$ is H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinato; and M is a chelated metal atom.

29. The compound of claim 28 wherein $R_{A1}$ has formula $C=C(R_D)$ provided that $R_D$ is not H or alkyl having 1 to about 20 carbon atoms.

30. The compound of claim 28 wherein $R_{A1}$ and $R_{A2}$ have formula $C=C(R_D)$.

31. The compound of claim 28 wherein $R_{A1}$ and $R_{A3}$ have formula $C=C(R_D)$ and $R_{A2}$ and $R_{A4}$ are not H.

32. The compound of claim 28 wherein $R_{A1}$, $R_{A2}$, and $R_{A3}$ have formula $C=C(R_D)$.

33. The compound of claim 28 wherein $R_{A1}$-$R_{A4}$ have formula $C=C(R_D)$ provided that $R_{B1}$-$R_{B8}$ are not H or alkyl having 1 to about 20 carbon atoms.

34. The compound of claim 28 wherein $R_{A1}$-$R_{A4}$ have formula $C=C(R_D)$ provided that $R_D$ is not H or trimethylsilyl.

35. A compound having formula (1) or (2):

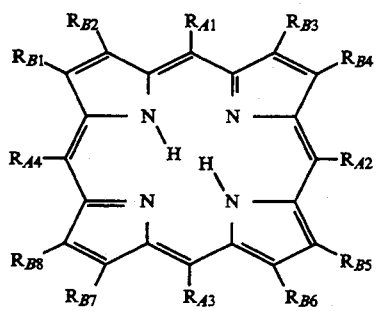

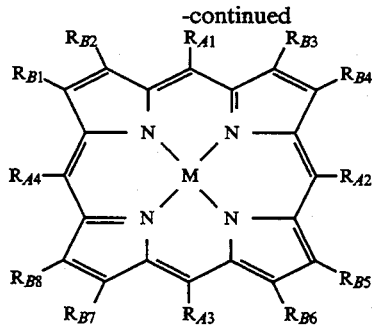

wherein:
(a) $R_{A1}$ has formula $C(R_C)=C(R_D)(R_E)$, provided that at least one of $R_C$, $R_D$, and $R_E$ is not H; or
(b) $R_{A1}$ and $R_{A2}$ have formula $C(R_C)=C(R_D)(R_E)$; or
(c) $R_{A1}$ and $R_{A3}$ have formula $C(R_C)=C(R_D)(R_E)$; or
(d) $R_{A1}$, $R_{A2}$, and $R_{A3}$ have formula $C(R_C)=C(R_D)(R_E)$; or
(e) $R_{A1}$-$R_{A4}$ have has formula $C(R_C)=C(R_D)(R_E)$, provided that at least one of $R_C$, $R_D$, and $R_E$ is not H and that $R_D$ and $R_E$ are not H, alkyl having from 1 to about 20 carbon atoms; or aryl having about 6 to about 20 carbon atoms; or
(f) $R_{A1}$-$R_{A4}$ have formula $C(R_C)=C(R_D)(R_E)$, provided that at least one of $R_C$, $R_D$, and $R_E$ is not H and that at east two of $R_{B1}$-$R_{B8}$ are not H;

where $R_C$, $R_D$, and $R_E$ are, independently, H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinato; and M is a chelated metal atom.

36. The compound of claim 35 wherein $R_{A1}$ has formula $C(R_C)=C(R_D)(R_E)$, provided that at least one of $R_C$, $R_D$, and $R_E$ is not H.

37. The compound of claim 35 wherein $R_{A1}$ and $R_{A2}$ have formula $C(R_C)=C(R_D)(R_E)$.

38. The compound of claim 35 wherein $R_{A1}$ and $R_{A3}$ have formula $C(R_C)=C(R_D)(R_E)$.

39. The compound of claim 35 wherein $R_{A1}$, $R_{A2}$, and $R_{A3}$ have formula $C(R_C)=C(R_D)(R_E)$.

40. The compound of claim 35 wherein $R_{A1}$-$R_{A4}$ have has formula $C(R_C)=C(R_D)(R_E)$, provided that at least one of $R_C$, $R_D$, and $R_E$ is not H and that $R_D$ and $R_E$ are not H, alkyl having from 1 to about 20 carbon atoms; or aryl having about 6 to about 20 carbon 41. The compound of claim 35 wherein $R_{A1}$-$R_{A4}$ have formula $C(R_C)=C(R_D)(R_E)$, provided that at least one of $R_C$, $R_D$, and $R_E$ is not H and that at least two of $R_{B1}$-$R_{B8}$ are not H.

42. The compound of claim 26 wherein $R_O$ is $C(R_C)=C(R_D)(R_E)$, $C=C(R_D)$, haloalkyl having from 1 to about 20 carbon atoms, or haloaryl having about 6 to about 20 carbon atoms, and $R_C$, $R_D$, and $R_E$ are, independently, H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinato.

43. The compound of claim 1 wherein at least one of $R_{A1}$-$R_{A4}$ has formula $C(R_C)=C(R_D)(R_E)$, provided that at least two of $R_C$, $R_D$ and $R_E$ are not H.

44. The compound of claim 1 wherein at least two of $R_{A1}$-$R_{A4}$ have formula $C(R_C)=C(R_D)(R_E)$, provided that at least one of $R_C$, $R_D$, and $R_E$ is not H.

* * * * *

UNITED STATES PATENT AND TRADEMARK OFFICE
CERTIFICATE OF CORRECTION

PATENT NO. : 5,371,199

DATED : 12/6/94

INVENTOR(S) : Michael J. Therien and Stephen G. DiMagno

It is certified that error appears in the above-indentified patent and that said Letters Patent is hereby corrected as shown below:

Column 2, lines 48-49, delete the second occasion of "at least"

Column 2, line 61, delete "$R_{A8}$" and insert $R_{A4}$"

Column 3, line 2, delete "and" and insert "aryl"

Column 7, line 30, add "$R_{A1}$" to the top of the lower porphyrin ring

Column 10, lines 29, 31, 45, and 49, replace the symbol "$\epsilon$" with "$\delta$"

Column 11, lines 2, 16, 19, 42, 64, and 66, replace the symbol "$\epsilon$" with "$\delta$"

Column 11, line 7, delete "110.59(0)" and insert "116.59(0)"

Column 11, line 67, delete the number "27.69" and insert "127.69" and delete the number "126,67" and insert "126.67"

Column 12, lines 17, 33, 39, 56 and 66, replace the symbol "$\epsilon$" with "$\delta$"

Column 12, line 45, delete the number "121.70(1)" and insert "124.70(1)"

Column 12, line 46, delete the number "113.15(1)" and insert "118.15(1)"

Column 12, line 59, after "(shoulder);" insert "559"

UNITED STATES PATENT AND TRADEMARK OFFICE
CERTIFICATE OF CORRECTION

PATENT NO. : 5,371,199

DATED : 12/6/94

INVENTOR(S) : Michael J. Therien and Stephen G. DiMagno

It is certified that error appears in the above-indentified patent and that said Letters Patent is hereby corrected as shown below:

Column 12, line 62, "Butyl zinc" should be one word --Butylzinc--.

Column 16, line 17, after "where" insert --$R_{A1}$--.

Column 19, claim 1, line 38, change "$C=C(R_D)$" to --$C\equiv C(R_D)$--.

Column 19, claim 1, line 47, Section (g) is missing from the patent as follows:
  --(g) at least one of $R_{B1}$ - $R_{B8}$ is haloaryl having about 6 to about 20 carbons atoms; or --

Column 19, claim 1, line 58, "porphyrinatol" should be --porphyrinato--.

Column 19, claim 4, line 66, change "$C=C(R_D)$" to --$C\equiv C(R_D)$--.

Column 20, claim 11, line 16, change "$C=C(R_D)$" to --$C\equiv C(R_D)$--.

Column 20, claim 12, line 20, change "$C=C(R_D)$" to --$C\equiv C(R_D)$--.

Column 20, claim 13, line 24, change "$C=C(R_D)$" to --$C\equiv C(R_D)$--.

Column 20, claim 14, line 28, change "$C=C(R_D)$" to --$C\equiv C(R_D)$--.

UNITED STATES PATENT AND TRADEMARK OFFICE
CERTIFICATE OF CORRECTION

PATENT NO. : 5,371,199

DATED : 12/6/94

INVENTOR(S) :
          Michael J. Therien and Stephen G. DiMagno

It is certified that error appears in the above-indentified patent and that said Letters Patent is hereby corrected as shown below:

Column 20, claim 16, line 35, change "$C=C(R_D)$" to --$C\equiv C(R_D)$--.

Column 20, claim 17, line 43, change "$C=C(R_D)$" to --$C\equiv C(R_D)$--.

Column 20, claim 19, line 56, change "$C=C(R_D)$" to --$C\equiv C(R_D)$--.

Column 21, claim 24, line 38, change "$C=C(R_D)$" to --$C\equiv C(R_D)$--.

Column 22, claim 26, line 50, "bout" is misspelled and should be --about--.

Column 23, claim 28, line 16, change "$C=C(R_D)$" to --$C\equiv C(R_D)$--.

Column 23, claim 28, line 20, change "$C=C(R_D)$" to --$C\equiv C(R_D)$--.

Column 23, claim 28, line 21, change "$C=C(R_D)$" to --$C\equiv C(R_D)$--.

Column 23, claim 28, line 23, change "$C=C(R_D)$" to --$C\equiv C(R_D)$--.

Column 23, claim 28, line 24, change "$C=C(R_D)$" to --$C\equiv C(R_D)$--.

UNITED STATES PATENT AND TRADEMARK OFFICE
CERTIFICATE OF CORRECTION

PATENT NO. : 5,371,199

DATED : 12/6/94

INVENTOR(S) :
Michael J. Therien and Stephen G. DiMagno

It is certified that error appears in the above-indentified patent and that said Letters Patent is hereby corrected as shown below:

Column 23, claim 28, line 28, change "C=C($R_D$)" to --C≡C($R_D$)--.

Column 23, claim 29, line 38, change "C=C($R_D$)" to --C≡C($R_D$)--.

Column 23, claim 30, line 41, change "C=C($R_D$)" to --C≡C($R_D$)--.

Column 23, claim 31, line 44, change "C=C($R_D$)" to --C≡C($R_D$)--.

Column 23, claim 32, line 46, change "C=C($R_D$)" to --C≡C($R_D$)--.

Column 23, claim 33, line 48, change "C=C($R_D$)" to --C≡C($R_D$)--.

Column 23, claim 34, line 52, change "C=C($R_D$)" to --C≡C($R_D$)--.

Column 24, claim 40, line 49, after "carbon" insert --atom.--

Column 24, claim 42, line 55, change "C=C($R_D$)" to --C≡C($R_D$)--.

UNITED STATES PATENT AND TRADEMARK OFFICE
CERTIFICATE OF CORRECTION

PATENT NO. : 5,371,199
DATED : 12/6/94
INVENTOR(S) : Michael J. Therien and Stephen G. DiMagno It is certified that error appears in the above-indentified patent and that said Letters Patent is hereby corrected as shown below:

Column 24, claim 42, line 55, change "$C=C(R_D)$" to --$C\equiv C(R_D)$--.

Signed and Sealed this

Twenty-second Day of August, 1995

Attest:

BRUCE LEHMAN

Attesting Officer    Commissioner of Patents and Trademarks

REEXAMINATION CERTIFICATE (2760th)

United States Patent [19]

Therien et al.

[11] B1 5,371,199

[45] Certificate Issued Dec. 26, 1995

[54] SUBSTITUTED PORPHYRINS, PORPHYRIN-CONTAINING POLYMERS, AND SYNTHETIC METHODS THEREFOR

[75] Inventors: Michael J. Therien; Stephen G. DiMagno, both of Philadelphia, Pa.

[73] Assignee: The Trustees of the University of Pennsylvania, Philadelphia, Pa.

Reexamination Request:
No. 90/003,838, May 22, 1995

Reexamination Certificate for:
Patent No.: 5,371,199
Issued: Dec. 6, 1994
Appl. No.: 929,943
Filed: Aug. 14, 1992

[51] Int. Cl.$^6$ .................. C07D 487/22; C01F 17/00; C01G 55/00
[52] U.S. Cl. .................. 534/11; 534/15; 540/145
[58] Field of Search .................. 540/145; 534/11, 534/15

[56] References Cited

U.S. PATENT DOCUMENTS

| | | | |
|---|---|---|---|
| 4,970,348 | 11/1990 | Ellis, Jr. et al. | 568/399 |
| 5,118,886 | 6/1992 | Ellis, Jr. et al. | 568/910 |
| 5,120,882 | 6/1992 | Ellis, Jr. et al. | 568/910 |
| 5,120,886 | 6/1992 | Lyons et al. | 568/909.8 |
| 5,212,300 | 5/1993 | Ellis, Jr. et al. | 540/145 |
| 5,280,115 | 1/1994 | Ellis, Jr. et al. | 540/145 |

FOREIGN PATENT DOCUMENTS

| | | |
|---|---|---|
| 0471561A2 | 2/1992 | European Pat. Off. . |
| 0494508A1 | 7/1992 | European Pat. Off. . |

OTHER PUBLICATIONS

Kaesler, et al., "Synthesis of (Polyfluoroalkyl)pyrroles and porphyrins," *J. Org. Chem.* 1982, 47(27), 5243–5246.

Hevesi, et al., "Synthesis of meso–Tetravinyl Porphyrins through 1–Selenoallyl Cationic Species", *J. Chem. Soc., Chem. Commun.*, 1986, 1725–1727.

Vincenti, et al., "Vilsmeier Reactions of Porphyrins . . . Using Low–Valent Titanium Complexes," *J. Org. Chem.* 1991, 56, 4407–4418.

Aoyagi, et al., "Facile Syntheses of Perfluoroalkylporphyrins. Electron Deficient Porphyrins II," *Chemistry Letters* 1988, 1891–1894.

*Primary Examiner*—Robert J. Bond

[57] ABSTRACT

Porphyrins substituted with, for example, vinyl and acetylene groups are provided, along with polymers containing the same. In preferred embodiments, the substituted porphyrins are prepared by coupling halogenated porphyrins with carbon-centered anionic groups via metal-mediated cross-coupling reactions under stoichiometric or catalytic conditions.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 24–34 and 42 is confirmed.

Claims 1, 3, 6–7, 35–39 and 43–44 are determined to be patentable as amended.

Claims 2, 4, 5, 8–23, 40 and 41, dependent on an amended claim, are determined to be patentable.

1. A compound having formula (1) or (2):

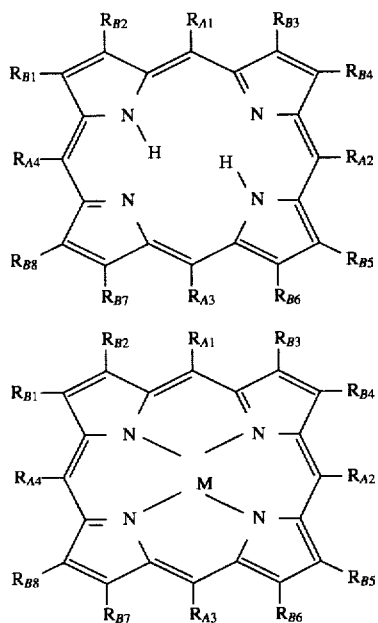

wherein:

(a) at least two of $R_{A1}$–$R_{A4}$ has formula $CH=CH_2$; or (b) at least one of $R_{B1}$–$R_{B8}$ has formula $C(R_C)=C(R_D)(R_E)$, provided that at least one of $R_C$, $R_D$, and $R_E$ is not H *and that $R_D$ and $R_E$ are not H and porphyrinato*; or (c) at least two of $R_{B1}$–$R_{B8}$ have formula $C=C(R_D)$; or (d) at least one of $R_{A1}$–$R_{A4}$ is haloalkyl having 1 to about 20 carbon atoms; or (e) at least [one] *five* of $R_{B1}$–$R_{B8}$ is [haloalkyl] *perhaloalkyl* having 2 to about 20 carbon atoms; or (f) at least five of $R_{B1}$–$R_{B8}$ are [haloalkyl] *perhaloalkyl* having 1 to about 20 carbon atoms or haloaryl having about 6 to about 20 carbon atoms; or (h) at least one of $R_{A1}$–$R_{A4}$ has formula $C(R_C)=C(R_D)(R_E)$, provided that at least two of $R_C$, $R_D$ and $R_E$ are not H *and that $R_D$ and $R_E$ are not both H, both alkyl, both aryl, H and aryl, or alkyl and aryl*;
or (i) at least two of $R_{A1}$–$R_{A4}$ have formula $C(R_C)=C(R_D)(R_E)$, provided that at least one of $R_C$, $R_D$, $R_E$ is not H *and that $R_D$ and $R_E$ are not both H, both alkyl, both aryl, H and aryl, or alkyl and aryl*;

where $R_C$, $R_D$, and $R_E$ are, independently, H, F, Cl, Br, I, alkyl having from 1 to about 20 carbon atoms, aryl, having about 6 to about 20 carbon atoms, alkenyl having from 1 to about 20 carbon atoms, alkynyl having from 1 to about 20 carbon atoms, trialkylsilyl, or porphyrinatol; and M is a chelated metal atom.

3. The compound of claim 1 wherein at least one of $R_{B1}$–$R_{B8}$ has formula $C(R_C)=C(R_D)(R_E)$, provided that at least one of $R_C$, $R_D$, and $R_E$ is not H *and that $R_D$ and $R_E$ are not H and porphyrinato*.

6. The compound of claim 1 wherein at least [one] *five* of $R_{B1}$–$R_{B8}$ is [haloalkyl] *perhaloalkyl* having 2 to about 20 carbon atoms.

7. The compound of claim 1 wherein at least five of $R_{B1}$–$R_{B8}$ are [haloalkyl] *perhaloalkyl* having from 1 to about 20 carbon atoms.

35. A compound having formula (1) or (2):

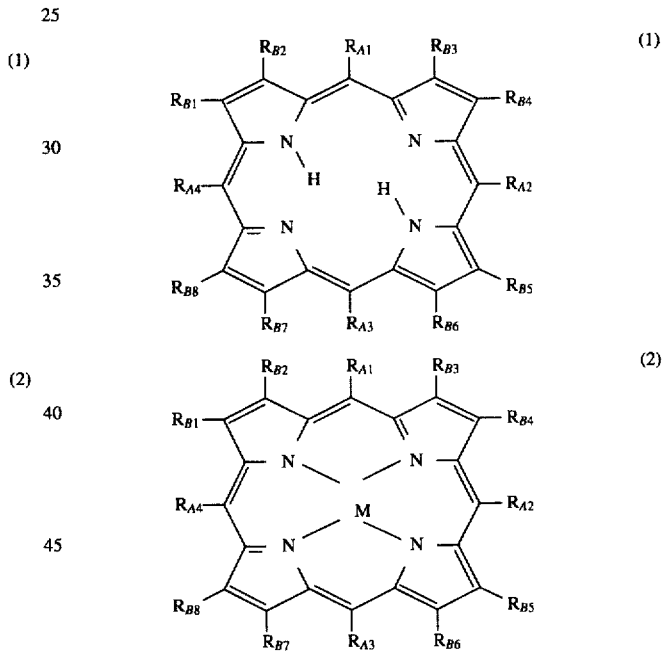

wherein:

(a) $R_{A1}$ has formula $C(R_C)=C(R_D)(R_E)$, provided that at least one of $R_C$, $R_D$, and $R_E$ is not H *and that $R_D$ and $R_E$ are not both H, both alkyl, both aryl, H and aryl, H and porphyrinato, or alkyl and aryl*; or (b) $R_{A1}$ and $R_{A2}$ have formula $C(R_C)=C(R_D)(R_E)$, provided that $R_D$ and $R_E$ are not both H, both aryl, H and aryl, or alkyl and aryl; or (c) $R_{A1}$ and $R_{A3}$ have formula $C(R_C)=C(R_D)(R_E)$, provided that $R_D$ and $R_E$ are not both H, both aryl, H and aryl, or alkyl and aryl; or (d) $R_{A1}$, $R_{A2}$, and $R_{A3}$ have formula $C(R_C)=C(R_D)(R_E)$, provided that $R_D$ and $R_E$ are not both H, both aryl, H and aryl, or alkyl and aryl; or (e) $R_{A1}$–$R_{A4}$ have has formula $C(R_C)=C(R_D)(R_E)$, provided that at least one of $R_C$, $R_D$, and $R_E$ is not H and that $R_D$ and $R_E$ are not H, alkyl having from 1 to about 20 carbon atoms; or aryl having about 6 to about 20 carbon atoms; or (f) $R_{A1}$–$R_{A4}$ have formula $C(R_C)=C(R_D)(R_E)$, provided that at least one of $R_C$, $R_D$, and $R_E$ is not H and that at east two of $R_{B1}$–$R_{B8}$ are not H;

where $R_C$, $R_D$, and $R_E$ are, independently, H, F, Cl, Br, I, alkyl having from 1 to about 20 carbon atoms, aryl having about 6 to about 20 carbon atoms, alkenyl having from 1 to about 20 carbon atoms, alkynyl having from 1 to about 20 carbon atoms, trialkylsilyl, or porphyrinato; and M is a chelated metal atom.

36. The compound of claim 35 wherein $R_{A1}$ has formula $C(R_C)=C(R_D)(R_E)$, provided that at least one of $R_C$, $R_D$, and $R_E$ is not H *and that $R_D$ and $R_E$ are not both H, both alkyl, both aryl, H and aryl, H and porphyrinato, or alkyl and aryl.*

37. The compound of claim 35 wherein $R_{A1}$ and $R_{A2}$ have formula $C(R_C)=C(R_D)(R_E)$, *provided that $R_D$ and $R_E$ are not both H, both alkyl, both aryl, H and aryl, or alkyl and aryl.*

38. The compound of claim 35 wherein $R_{A1}$ and $R_{A3}$ have formula $C(R_C)=C(R_D)(R_E)$, *provided that $R_D$ and $R_E$ are not both H, both alkyl, both aryl, H and aryl, or alkyl and aryl.*

39. The compound of claim 35 wherein $R_{A1}$, $R_{A2}$, and $R_{A3}$ have formula $C(R_C)=C(R_D)(R_E)$, *provided that $R_D$ and $R_E$ are not both H, both alkyl, both aryl, H and aryl, or alkyl and aryl.*

43. The compound of claim 1 wherein at least one of $R_{A1}$–$R_{A4}$ has formula $C(R_C)=C(R_D)(R_E)$, provided that at least two of $R_C$, $R_D$ and $R_E$ are not H *and that $R_D$ and $R_E$ are not both H, both alkyl, both aryl, H and aryl, or alkyl and aryl.*

44. The compound of claim 1 wherein at least two of $R_{A1}$–$R_{A4}$ have formula $C(R_C)=C(R_D)(R_E)$, provided that at least one of $R_C$, $R_D$, and $R_E$ is not H *and that $R_D$ and $R_E$ are not both H, both alkyl, both aryl, H and aryl, or alkyl and aryl.*

\* \* \* \* \*